US012679866B2

(12) United States Patent
Koga

(10) Patent No.: US 12,679,866 B2
(45) Date of Patent: Jul. 14, 2026

(54) PEPTIDE, AND CELL FUSION AGENT AND PHARMACEUTICAL COMPOSITION FOR CANCER THERAPY CONTAINING SAID PEPTIDE

(71) Applicant: Michiko Koga, Shizuoka (JP)

(72) Inventor: Michiko Koga, Shizuoka (JP)

( * ) Notice: Subject to any disclaimer, the term of this patent is extended or adjusted under 35 U.S.C. 154(b) by 813 days.

(21) Appl. No.: 17/753,919

(22) PCT Filed: Sep. 18, 2020

(86) PCT No.: PCT/JP2020/035491
§ 371 (c)(1),
(2) Date: Mar. 18, 2022

(87) PCT Pub. No.: WO2021/054448
PCT Pub. Date: Mar. 25, 2021

(65) Prior Publication Data
US 2023/0034205 A1      Feb. 2, 2023

(30) Foreign Application Priority Data
Sep. 20, 2019      (JP) ................................. 2019-171919

(51) Int. Cl.
| | |
|---|---|
| *C07K 7/06* | (2006.01) |
| *A61P 35/00* | (2006.01) |
| *C07K 16/44* | (2006.01) |
| *A61K 38/00* | (2006.01) |
| *A61K 48/00* | (2006.01) |

(52) U.S. Cl.
CPC ................ *C07K 7/06* (2013.01); *A61P 35/00* (2018.01); *C07K 16/44* (2013.01); *A61K 38/00* (2013.01); *A61K 48/00* (2013.01)

(58) Field of Classification Search
CPC . C07K 7/06; C07K 16/44; C07K 7/08; C07K 16/00; A61P 35/00; A61K 38/00; A61K 48/00
See application file for complete search history.

(56) References Cited

U.S. PATENT DOCUMENTS

| | | | |
|---|---|---|---|
| 2008/0176923 | A1 | 7/2008 | Salama |
| 2009/0280534 | A1 | 11/2009 | Christensen et al. |
| 2010/0173404 | A1 | 7/2010 | Kumon et al. |

FOREIGN PATENT DOCUMENTS

| | | |
|---|---|---|
| CN | 101541960 A | 9/2009 |
| CN | 107201344 A | 9/2017 |
| CN | 108315319 A | 7/2018 |
| CN | 108707600 A | 10/2018 |
| EP | 0128567 A2 | 12/1984 |
| EP | 0594282 A2 | 4/1994 |
| EP | 1454988 A1 | 9/2004 |
| JP | 5768790 A | 4/1982 |
| JP | 2007523829 A | 8/2007 |
| JP | 2008523829 A | 7/2008 |
| WO | WO-2010011347 A2 * | 1/2010 ............. A61K 38/08 |

OTHER PUBLICATIONS

N-Methyl Amino Acids Archives, AAPPTEC, published online 2012.*
Uniprot Protein Database, A0A4V6DIC8 · A0A4V6DIC8_9PEZI, accessed on Jan. 23, 2025, Icb1—Serine palmitoyltransferase 1—Colletotrichum tanaceti | UniProtKB | UniProt.*
JM Gasent Blesa, Cell-cell fusion as a potential target in cancer therapy , ecancer 2009, 3:145, pp. 1-9.*
Uniprot Protein Database, A0A2P4WXR1, Phytophthora palmivora, May 23, 2018.*
Harris, "Cell Fusion", pp. 1-10. 1970.
International Search Report and Written Opinion issued in PCT/JP2020/035491 (10 pages) Oct. 12, 2020.
Majorek et al. "Structural and Immunologic Characterization of Bovine, Horse and Rabbit Serum Albumins", Mol Immunol. Vol. 52(3-4), pp. 174-182. Oct. 2012.
Van De Sande et al. "Albumin-based Cancer Therapeutics for Intraperitoneal Drug Delivery: a Review", Drug Delivery, vol. 27, No. 1, pp. 40-53. 2020.
Zhao et al. "Preparation, Characterization, and in vitro Targeted Delivery of Folate-Decorated Paclitaxel-Loaded Bovine Serum Albumin Nanoparticles", International Journal of Nanomedicine, vol. 5, pp. 669-677. Sep. 10, 2010.
Hoogenboezem et al. "Harnessing Albumin as a Carrier for Cancer Therapies", Adv. Drug Deliv Rev., pp. 73-89. May 2018.
Ali et al. "Phytophthora megakarya and Phytophthora palmivora, Closely Related Casual Agents of Cacao Black Pod Rot, Underwent Increases in Genome Sizes and Gene Nos. by Different Mechanisms", Genome Biol. Evol., pp. 1-22. Feb. 2017.
Ali et al., *"Phytophthora palmivora* Var. Palmivora Strain SBR112.9 Scaffold 20380 Whole Genome Shotgun Sequence", GenBank: NCKW01020374.1, www.ncbi.nlm.nih.gov/nuccore/1338237519?sat=37&satkey=317198323, 8 pages. 2018.
Jeno et al. "Epitope Mapping of Bovine Serum Albumin Using Monoclonal Antibodies Coupled with a Photoreactive Crosslinker" J. Biochem, vol. 115, pp. 1119-1127. 1994.
Takaguchi, "A Single Amino Acid Mutation at Position 170 of Human Parainfluenza Virus Type 1 Fusion Glycoprotein Induces Obvious Syncytium Formation and Caspase-3-dependent Cell Death", The Journal of Biochemistry, 5 pages with abstract. 2011.
Gordon, "Cell Fusion and Some Subcellular Properties of Heterokaryons and Hybrids", The Journal of Cell Biology, vol. 67, pp. 257-280. 1975.

(Continued)

*Primary Examiner* — Erinne R Dabkowski
(74) *Attorney, Agent, or Firm* — Heslin Rothenberg Farley & Mesiti P.C.

(57) ABSTRACT

An object of the present invention is to provide an efficient method of cell fusion, and to provide a method of killing cancer cells by cell fusion. The object can be solved by (1) a polypeptide comprising an amino acid sequence selected from the group consisting of the amino acid sequences of SEQ ID NOs: 1 to 8, or (2) a polypeptide comprising an amino acid sequence, in which 1 to 4 amino acids are deleted, substituted, inserted, and/or added in an amino acid sequence of SEQ ID NOs: 1 to 8, and having a cell fusion activity.

8 Claims, 16 Drawing Sheets

Specification includes a Sequence Listing.

(56)  References Cited

OTHER PUBLICATIONS

Extended European Search Report in EP 20865680.1, 10 p. Nov. 21, 2023.

Summers et al., "Flaviviruses Can Mediate Fusion From Without in Aedes Albopictus Mosquito Cell Cultures", Virus Research, vol. 12, pp. 383-392. 1989.

Wang et al., "The Influence of New Medium wiht RGD on Cell Growth, Cell Fusion and Expression of Exogenous Gene", J. Sichuan Univ (Med Sci Edi), vol. 49(2), pp. 200-204, with abstract. 2018.

* cited by examiner (A)

(B)

(C)

(D)

(A)

(B)

(A)

(B)

(C)

(D)

(A)

(B)

(A)

(B)

(C)

(D)

(A) Caspase3/7-Green (B) AnnexinV-Red

Figure 16

□ Control group    ▨ Peptide 6 group 1534.88

925.7166667

Tumor weight (mg)

(Mean ± S.D.)

(A)　　　　　　　　　　　　　　　(B)

(C)　　　　　　　　　　　　　　　(D)

SEQUENCE LISTING

<160> NUMBER OF SEQ ID NOS: 9

<210> SEQ ID NO 1
<211> LENGTH: 10
<212> TYPE: PRT
<213> ORGANISM: Unknown
<220> FEATURE:
<223> OTHER INFORMATION: Fusion peptide

<400> SEQUENCE: 1

Pro Leu Val Ser Thr Gln Thr Ala Ile Ala
1               5                   10

<210> SEQ ID NO 2
<211> LENGTH: 10
<212> TYPE: PRT
<213> ORGANISM: Unknown
<220> FEATURE:
<223> OTHER INFORMATION: Fusion peptide

<400> SEQUENCE: 2

Pro Leu Val Ser Thr Gln Thr Ala Leu Ala
1               5                   10

<210> SEQ ID NO 3
<211> LENGTH: 10
<212> TYPE: PRT
<213> ORGANISM: Unknown
<220> FEATURE:
<223> OTHER INFORMATION: Fusion peptide

<400> SEQUENCE: 3

Pro Leu Val Ser Gln Thr Thr Ala Ile Ala
1               5                   10

<210> SEQ ID NO 4
<211> LENGTH: 10
<212> TYPE: PRT
<213> ORGANISM: Unknown
<220> FEATURE:
<223> OTHER INFORMATION: Fusion peptide

<400> SEQUENCE: 4

Pro Leu Val Ser Gln Thr Thr Ala Leu Ala
1               5                   10

<210> SEQ ID NO 5
<211> LENGTH: 10
<212> TYPE: PRT
<213> ORGANISM: Unknown
<220> FEATURE:
<223> OTHER INFORMATION: Fusion peptide

<400> SEQUENCE: 5

Pro Ile Val Ser Thr Gln Thr Ala Ile Ala
1               5                   10

<210> SEQ ID NO 6
<211> LENGTH: 10
<212> TYPE: PRT
<213> ORGANISM: Unknown
<220> FEATURE:
<223> OTHER INFORMATION: Fusion peptide

<400> SEQUENCE: 6

Pro Ile Val Ser Thr Gln Thr Ala Leu Ala
1               5                   10

-continued

```
<210> SEQ ID NO 7
<211> LENGTH: 10
<212> TYPE: PRT
<213> ORGANISM: Unknown
<220> FEATURE:
<223> OTHER INFORMATION: Fusion peptide

<400> SEQUENCE: 7

Pro Ile Val Ser Gln Thr Thr Ala Ile Ala
1               5                   10

<210> SEQ ID NO 8
<211> LENGTH: 10
<212> TYPE: PRT
<213> ORGANISM: Unknown
<220> FEATURE:
<223> OTHER INFORMATION: Fusion peptide

<400> SEQUENCE: 8

Pro Ile Val Ser Gln Thr Thr Ala Leu Ala
1               5                   10

<210> SEQ ID NO 9
<211> LENGTH: 12
<212> TYPE: PRT
<213> ORGANISM: Unknown
<220> FEATURE:
<223> OTHER INFORMATION: Fusion peptide

<400> SEQUENCE: 9

Pro Leu Val Ser Thr Gln Thr Ala Ile Ala Thr Ala
1               5                   10
```

PEPTIDE, AND CELL FUSION AGENT AND PHARMACEUTICAL COMPOSITION FOR CANCER THERAPY CONTAINING SAID PEPTIDE

CROSS REFERENCE TO RELATED APPLICATIONS

This application is a U.S. National Phase filing under 35 U.S.C. § 371 of International Application PCT/JP2020/035491, filed Sep. 18, 2020, and published as WO 2021/054448 A1 on Mar. 25, 2021. PCT/JP2020/035491 claims priority from Japanese application number 2019-171919, filed Sep. 20, 2019. The entire contents of each of these prior applications are hereby incorporated herein by reference.

SEQUENCE LISTING

The instant application contains a Sequence Listing, created on Sep. 15, 2022; the file, in ASCII format, is designated H2461193 and is 1,920 bytes in size. The file is hereby incorporated by reference in its entirety into the instant application.

TECHNICAL FIELD

The present invention relates to a peptide, and cell fusion agent and pharmaceutical composition for treating cancer comprising the same. According to the present invention, cells can be efficiently fused.

BACKGROUND ART

The cell fusion was found by the phenomenon that Sendai virus has the effect of fusing cells (Non-patent literatures 1 and 2). The cell fusion is recently used for breeding of plants, preparing monoclonal antibodies, or the like. It is known that the cell fusion is occurred by a protoplast, a PEG method, or an electrical stimulation, in addition to the use of the virus.

CITATION LIST

Non-Patent Literature

[NON-PATENT LITERATURE 1] Cell fusion, 1970, Harvard University Press, Mass.
[NON-PATENT LITERATURE 2] Cell Fusion and some subcellular Properties of heterokaryons and hybrids, Journal of Cell Biology, VOLUME 67, 1975, pages 257-280

SUMMARY OF INVENTION

Technical Problem

The present inventors have conducted studies on a method that can efficiently fuse cells, and have thought that the cell fusion could kill cancer cells.

Therefore, an object of the present invention is to provide an efficient method of cell fusion, and to provide a method of killing cancer cells by cell fusion.

Solution to Problem

The present inventors have conducted intensive studies into a method for efficiently fusing cells, as a result, surprisingly found that the cells can be fused by novel peptides having particular amino acid sequence.

The present invention is based on the above findings. Accordingly, the present invention relates to:

[1] (1) A polypeptide comprising an amino acid sequence selected from the group consisting of the amino acid sequences of SEQ ID NOs: 1 to 8, or (2) a polypeptide comprising an amino acid sequence, in which 1 to 4 amino acids are deleted, substituted, inserted, and/or added in an amino acid sequence of SEQ ID NOs: 1 to 8, and having a cell fusion activity,

[2] the polypeptide of the item [1], wherein the amino acid sequence of SEQ ID NOs: 1 to 8 has methyl group at the N-terminus thereof,

[3] a polynucleotide encoding the polypeptide of the item [1] or [2],

[4] a vector comprising the polynucleotide of the item [3],

[5] a transformant comprising the vector of the item [4],

[6] an antibody or an antigen binding fragment thereof, binding to the polypeptide of the item [1] or [2],

[7] a cell fusion agent comprising the polypeptide of the item [1] or [2], as an active ingredient,

[8] a pharmaceutical composition comprising the polypeptide of the item [1] or [2], as an active ingredient,

[9] the pharmaceutical composition of the item [8], for treating cancer,

[10] a method for treating cancer, comprising a step of administrating to a subject in need of such treatment a therapeutically effective amount of the polypeptide of the item [1] or [2],

[11] the polypeptide of the item [1] or [2], for treating cancer, and

[12] a use of the polypeptide of the item [1] or [2], for manufacturing a pharmaceutical composition for treating cancer.

Advantageous Effects of Invention

According to the polypeptide of the present invention, the cells can be efficiently fused. In addition, the polypeptide of the present invention can be used as an active ingredient of the pharmaceutical composition for treating cancer.

BRIEF DESCRIPTION OF THE DRAWINGS

FIG. 1-2 is micrographs of RFL cells (C (high magnification)) and LCC cells (D), in the case of the treatment of RFL cells and LCC cells by a peptide 1.

FIG. 2 is micrographs of RFL cells (A (low magnification) and B (high magnification)) in the case of the treatment of RFL cells by a peptide 2.

6-1 is micrographs of RFL cells (A (low magnification) and B (high magnification)) in the case of the treatment of RFL cells and RM-4 cells by a peptide 6.

Figure 2:
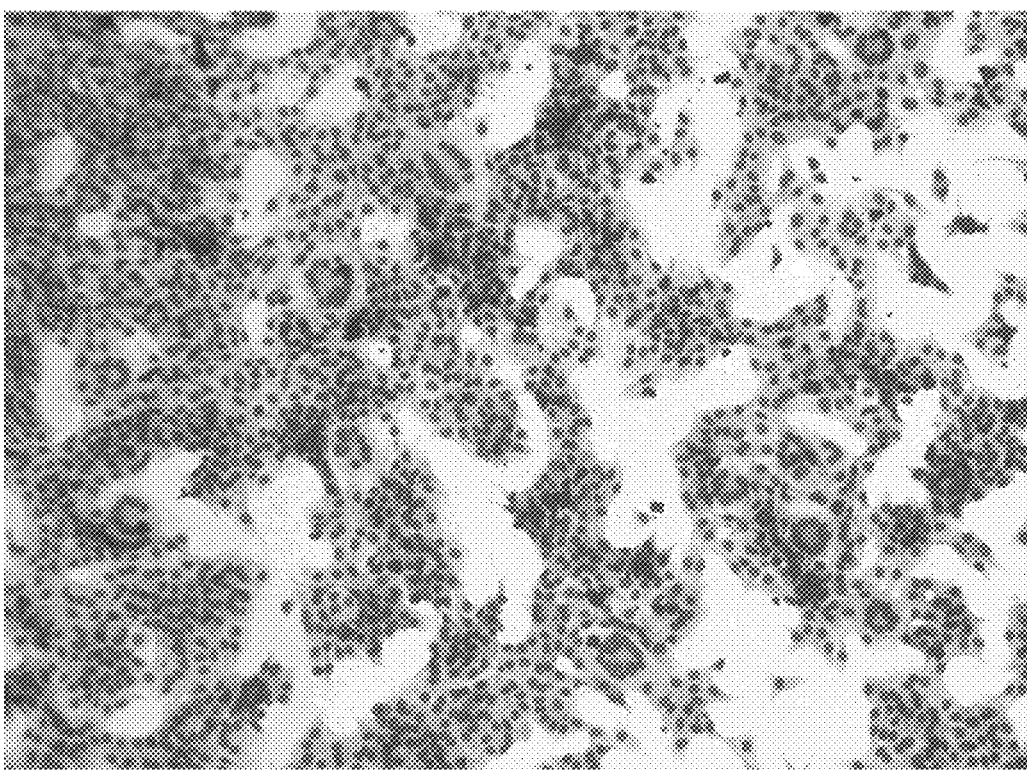
Figure 2:
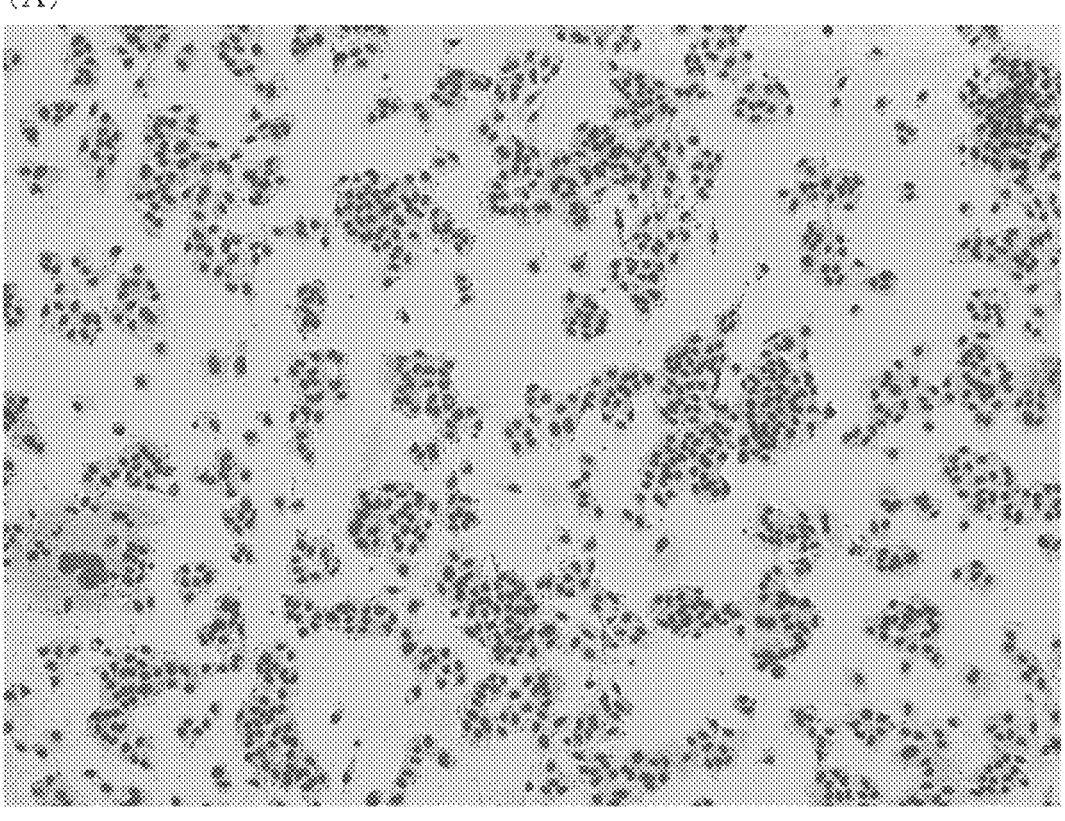
Figure 2:
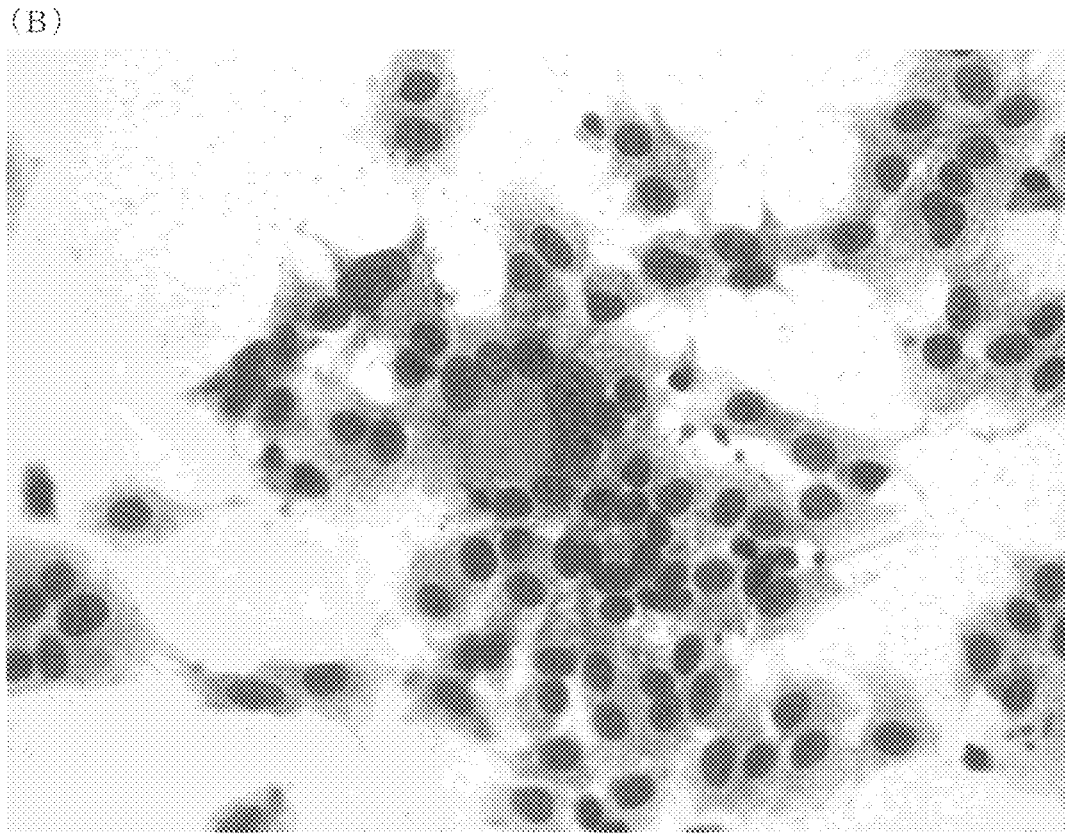
Figure 6:
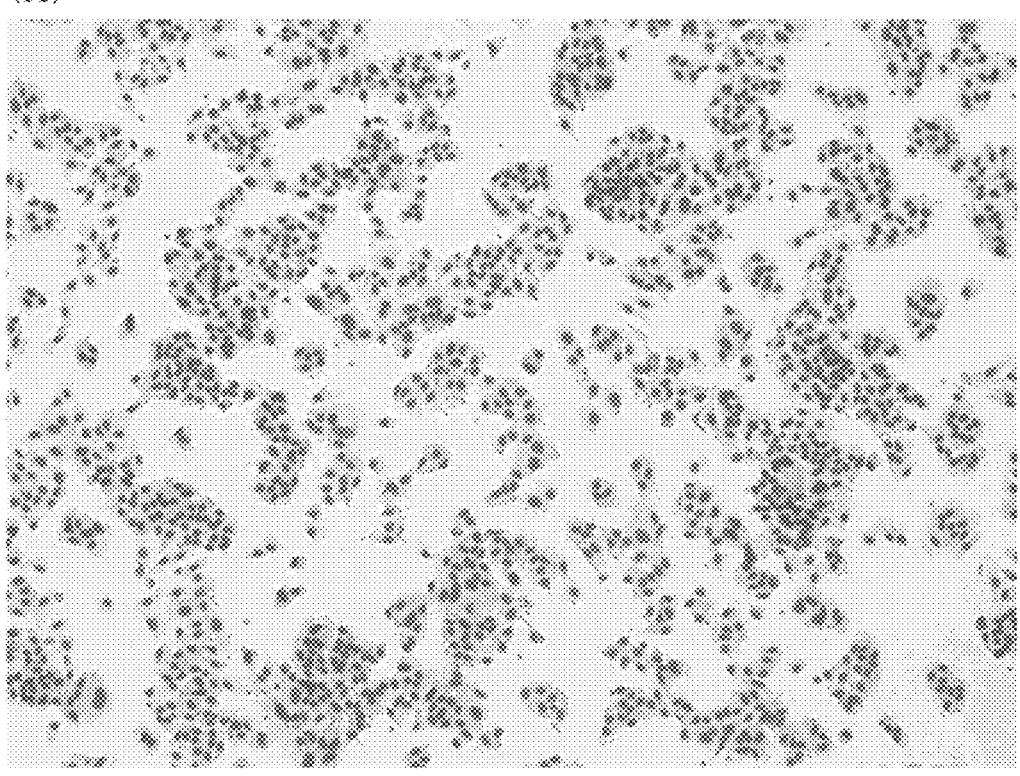
Figure 1:
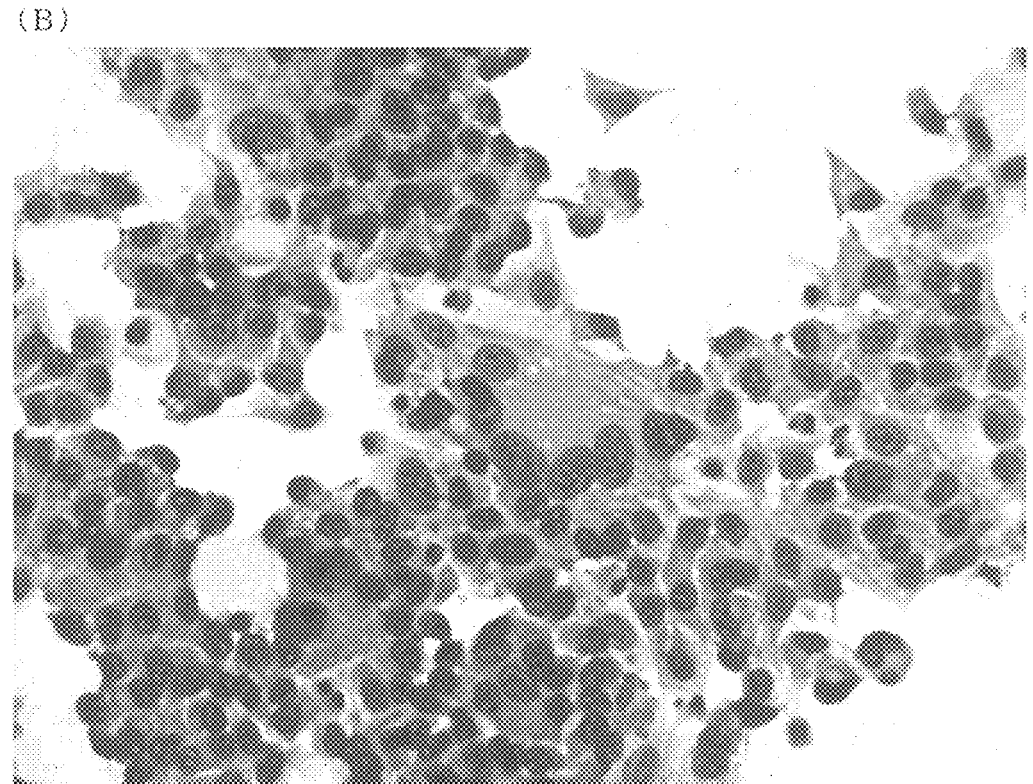
Figure 6:
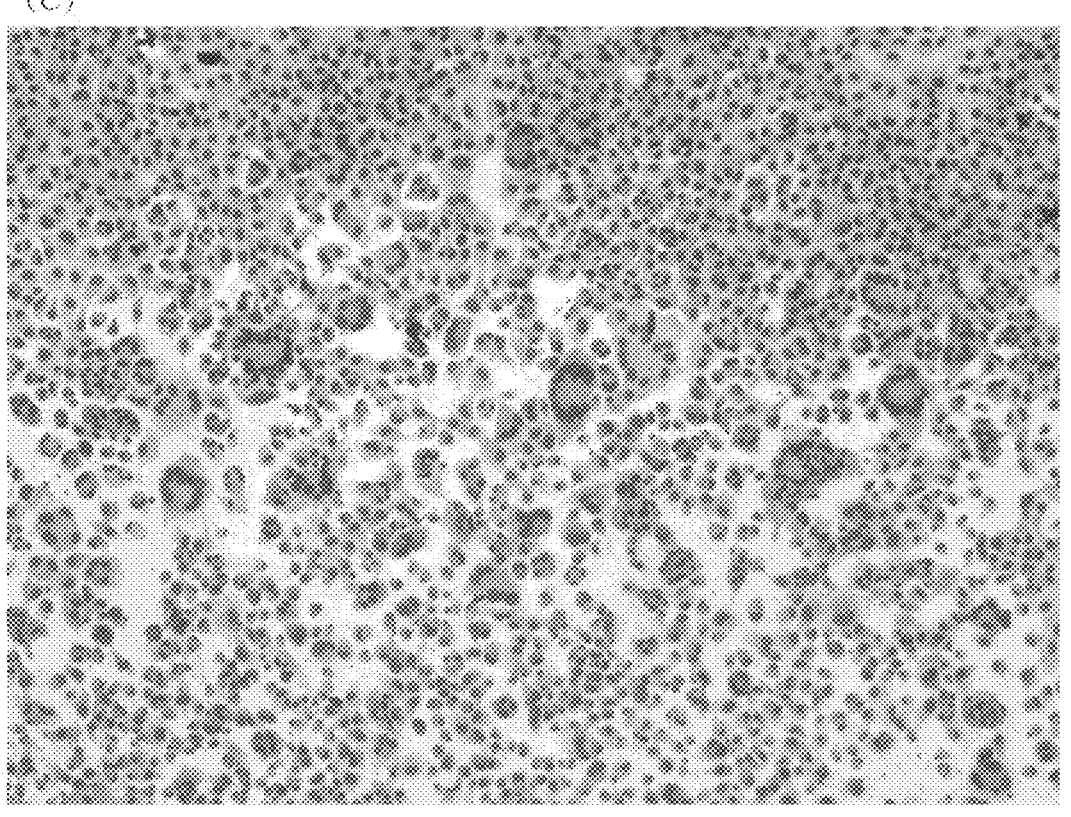
Figure 2:
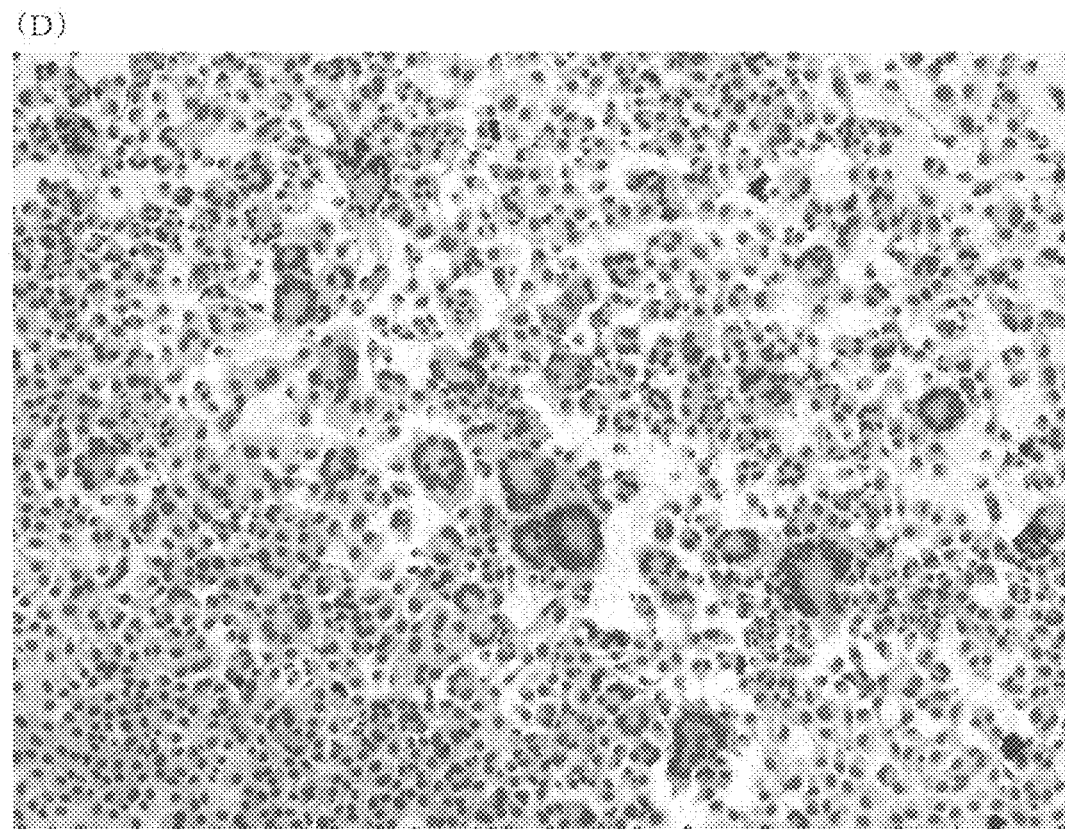

FIG. 6-2 is micrographs of RM-4 cells (C and D (low magnification)) in the case of the treatment of RFL cells and RM-4 cells by a peptide 6.

3

Figure 7:
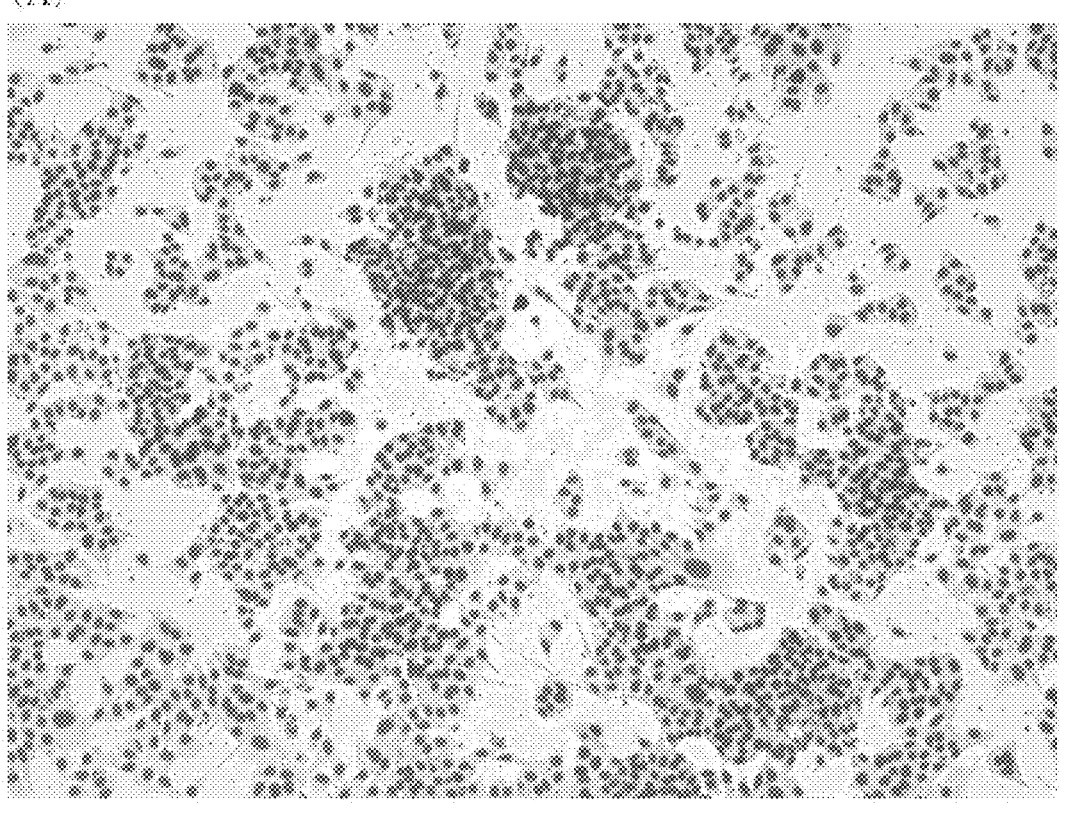
Figure 7:
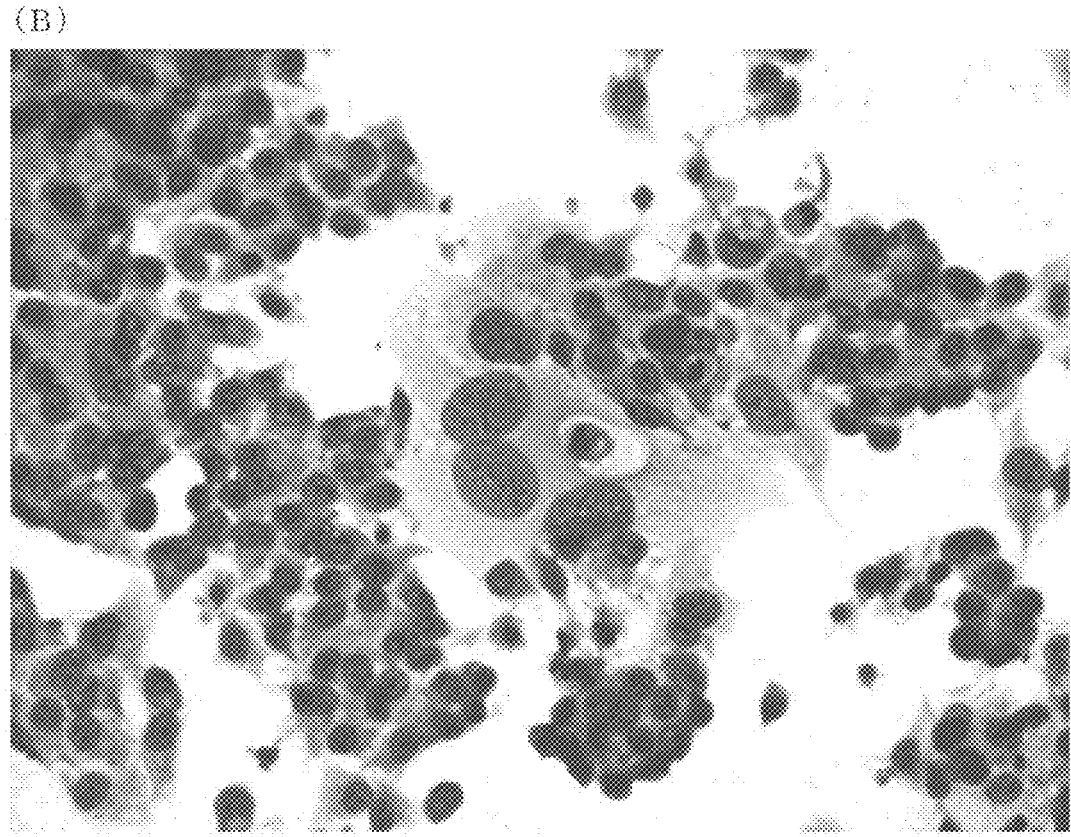

FIG. 7 is micrographs of RFL cells (A (low magnification) and B (high magnification)) in the case of the treatment of RFL cells by a peptide 7.

Figure 1:
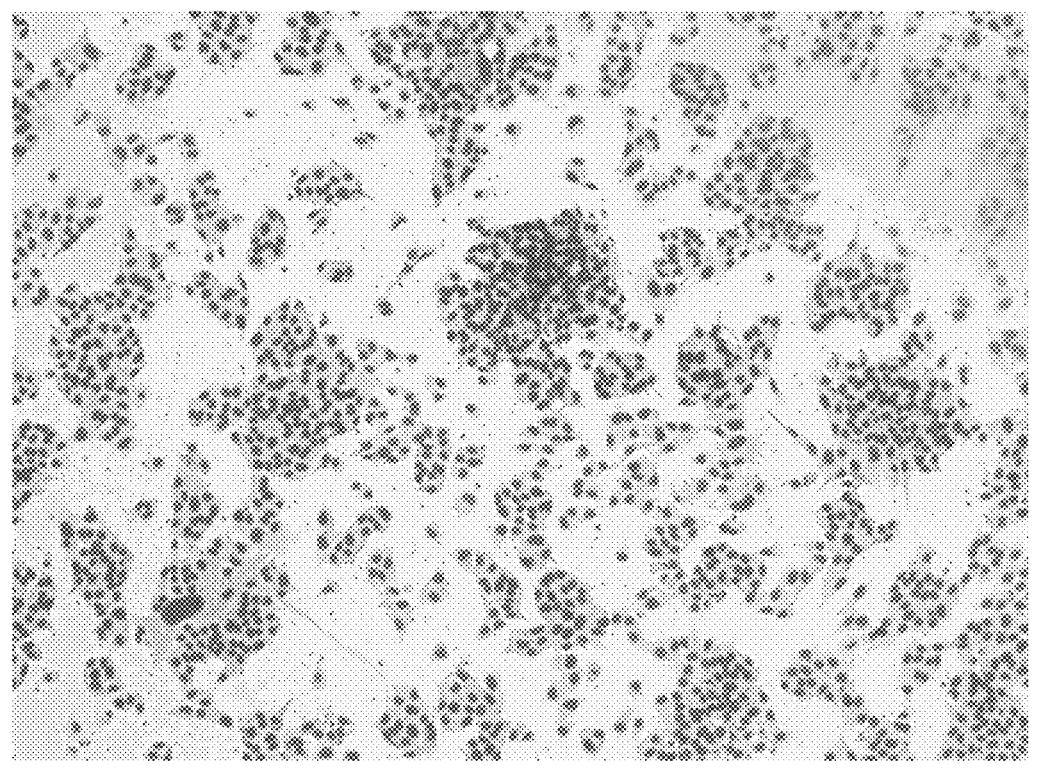
FIG. 1-1 is micrographs of RFL cells (A and B (low magnification)) in the case of the treatment of RFL cells and LCC cells by a peptide 1.
Figure 1:
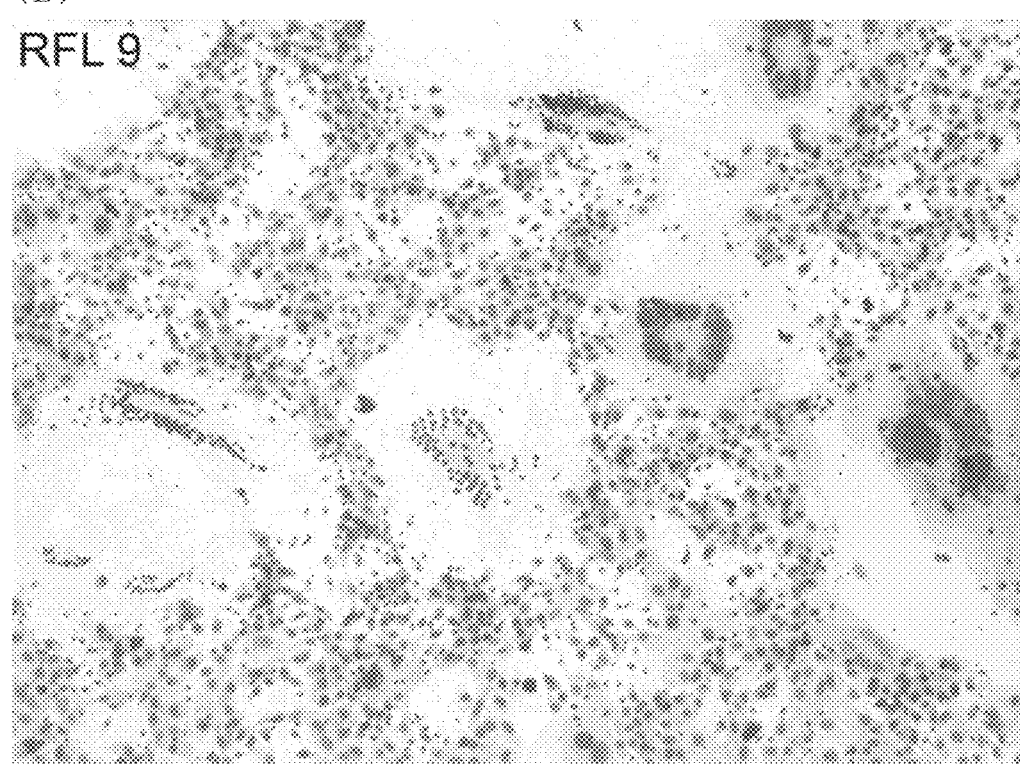
Figure 1:
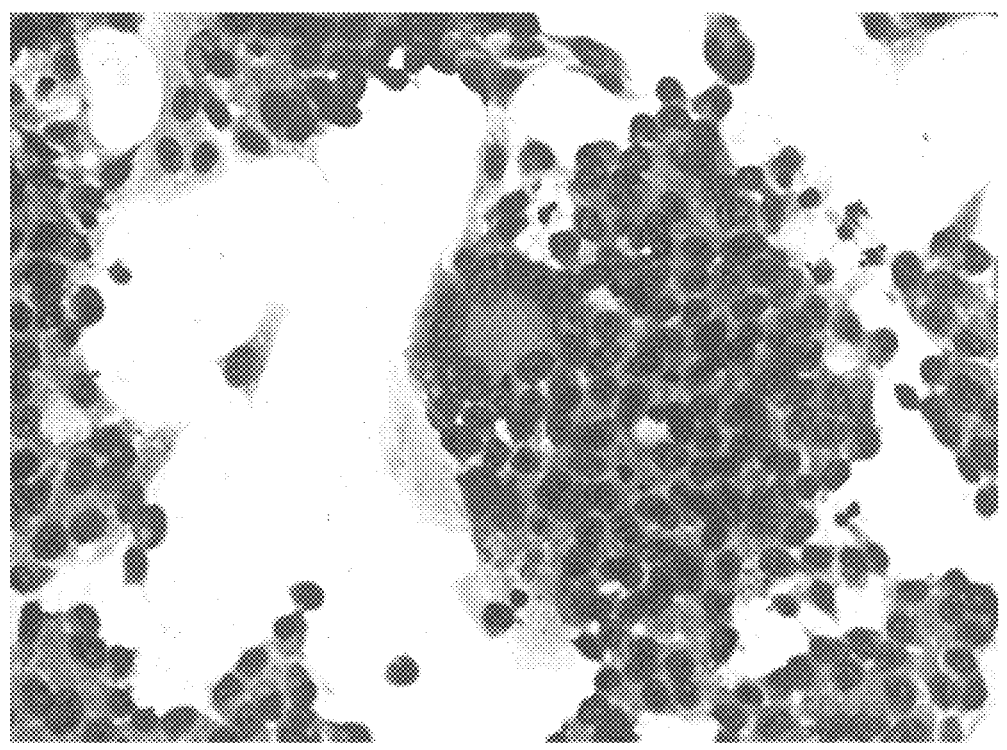
Figure 8:
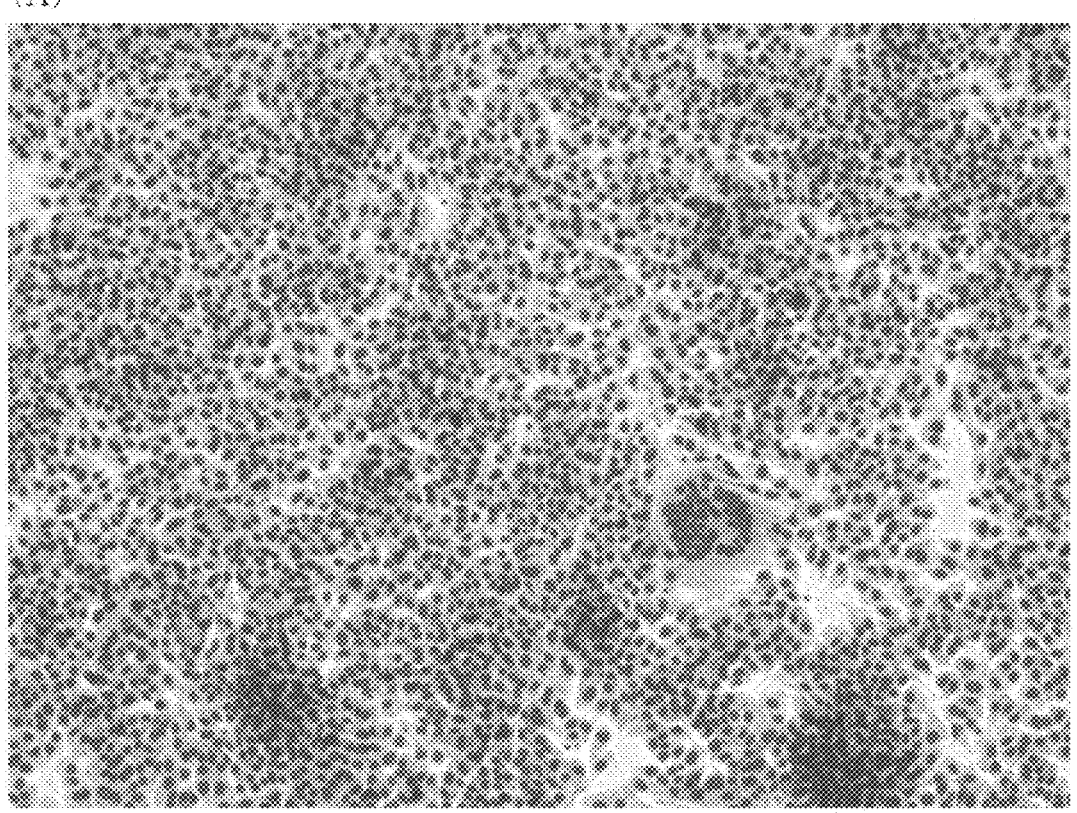
Figure 1:
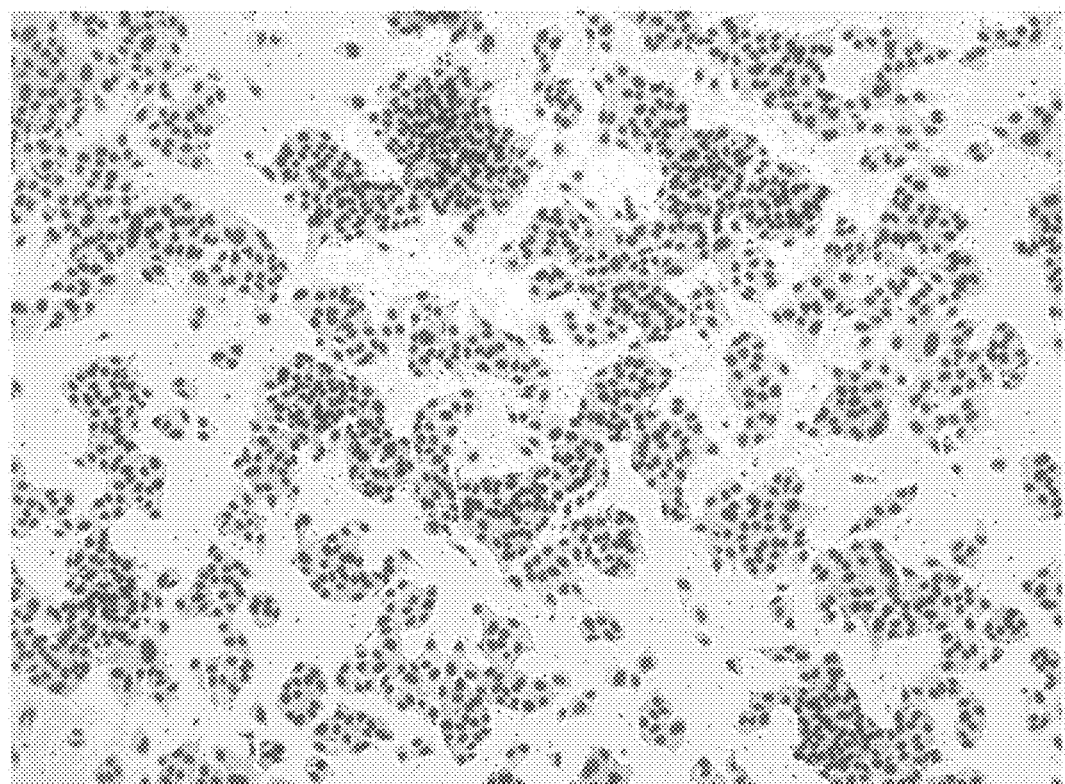
Figure 8:
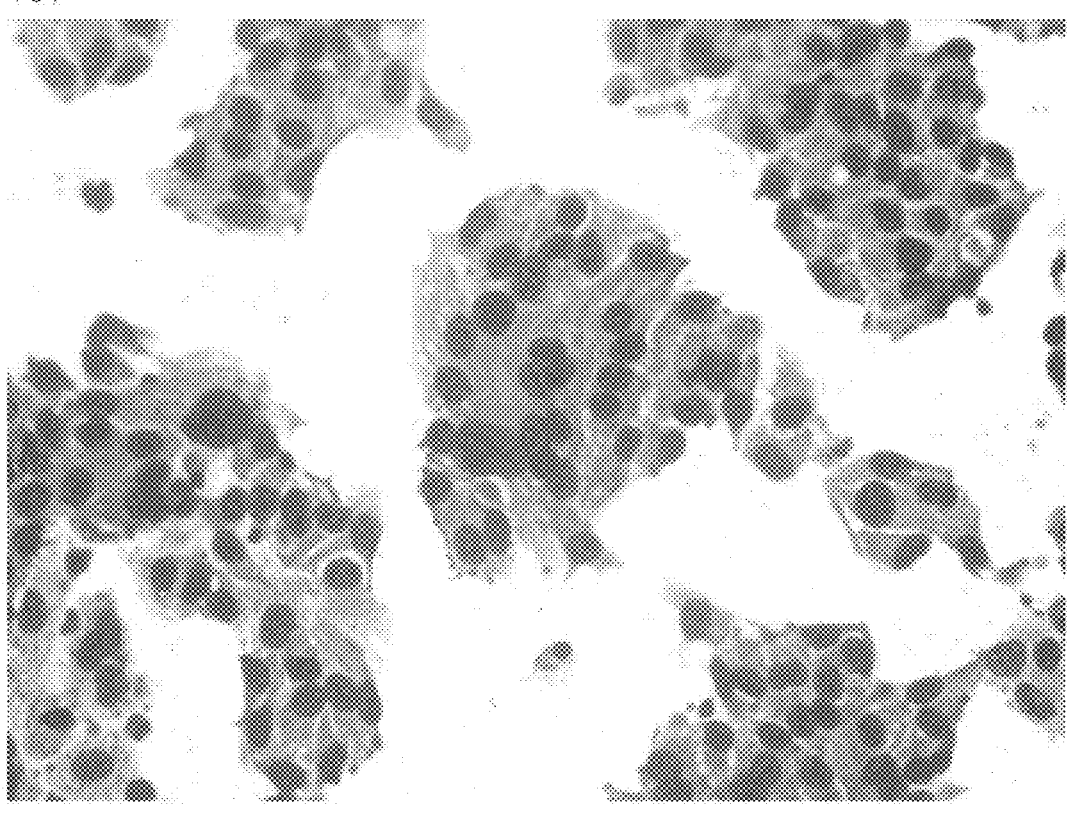
Figure 2:
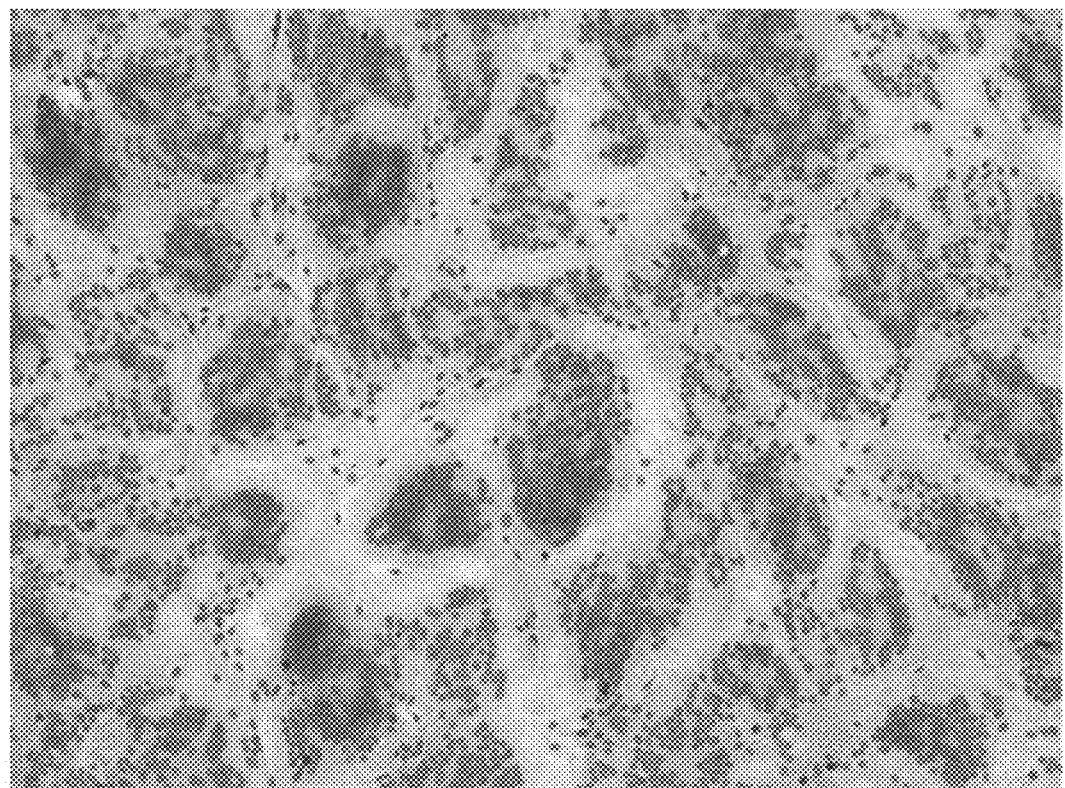

FIG. 8-1 is micrographs of RFL cells (A and B (low magnification)) in the case of the treatment of RFL cells and LCC cells by a peptide 8.

FIG. 8-2 is micrographs of RFL cells (C (high magnification)) and LCC cells (D), in the case of the treatment of RFL cells and LCC cells by a peptide 8.

Figure 9:
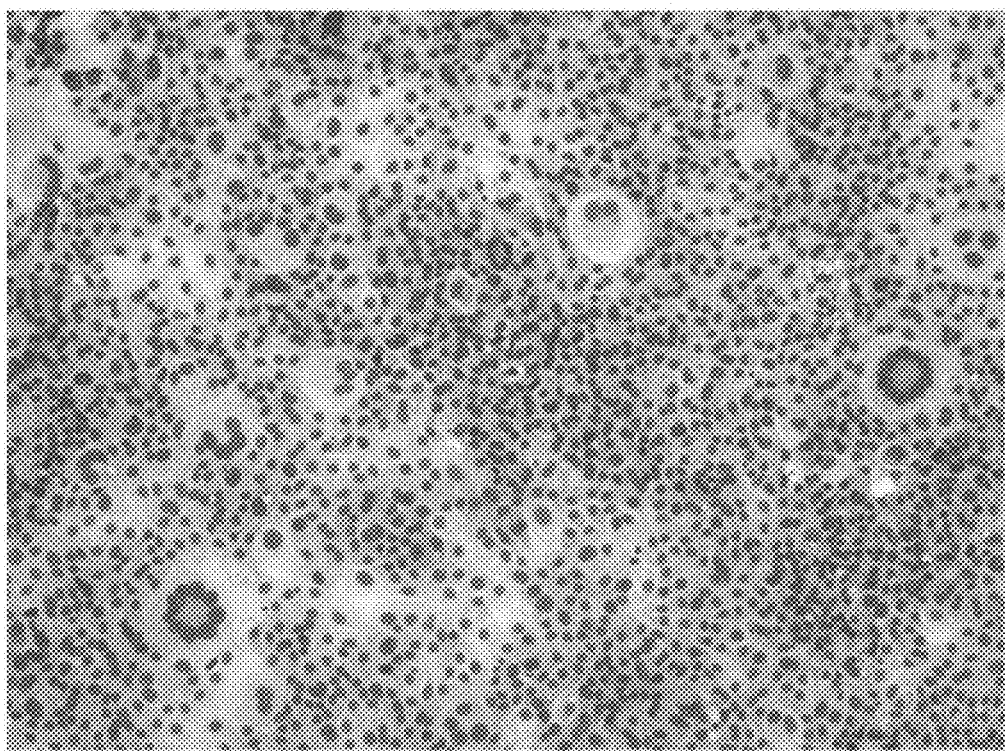

FIG. 9 is a micrograph of RFL cells (low magnification) in the case of the treatment of RFL cells by a peptide 9.

Figure 10:
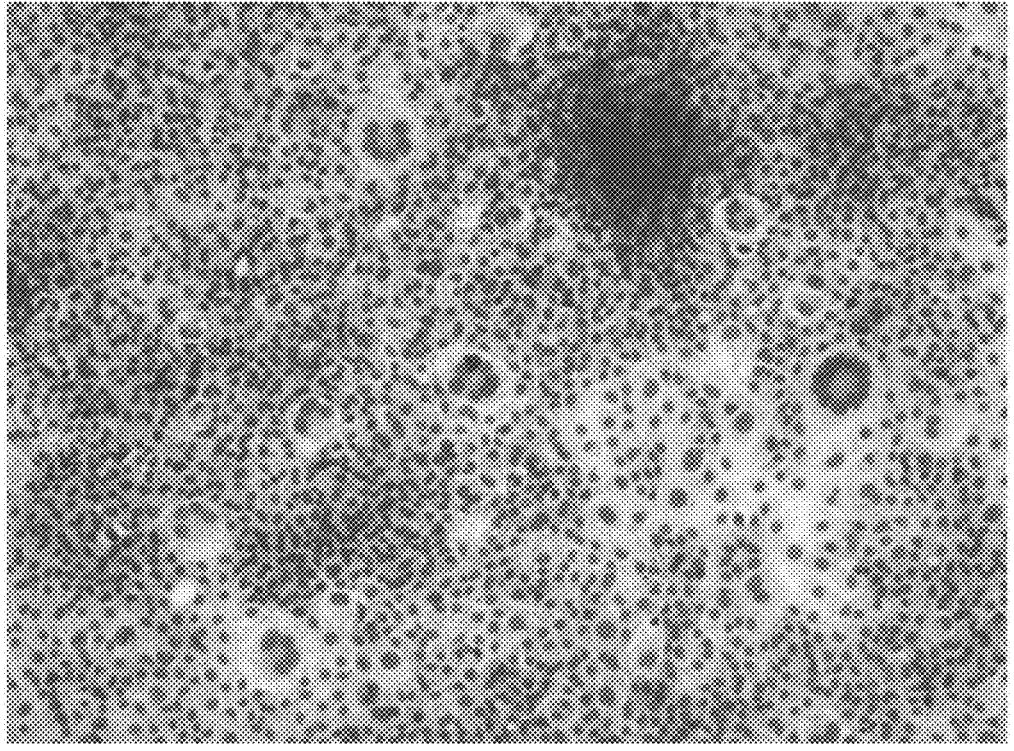

FIG. 10 is a micrograph of RFL cells (low magnification) in the case of the treatment of RFL cells by a peptide 10.

Figure 11:
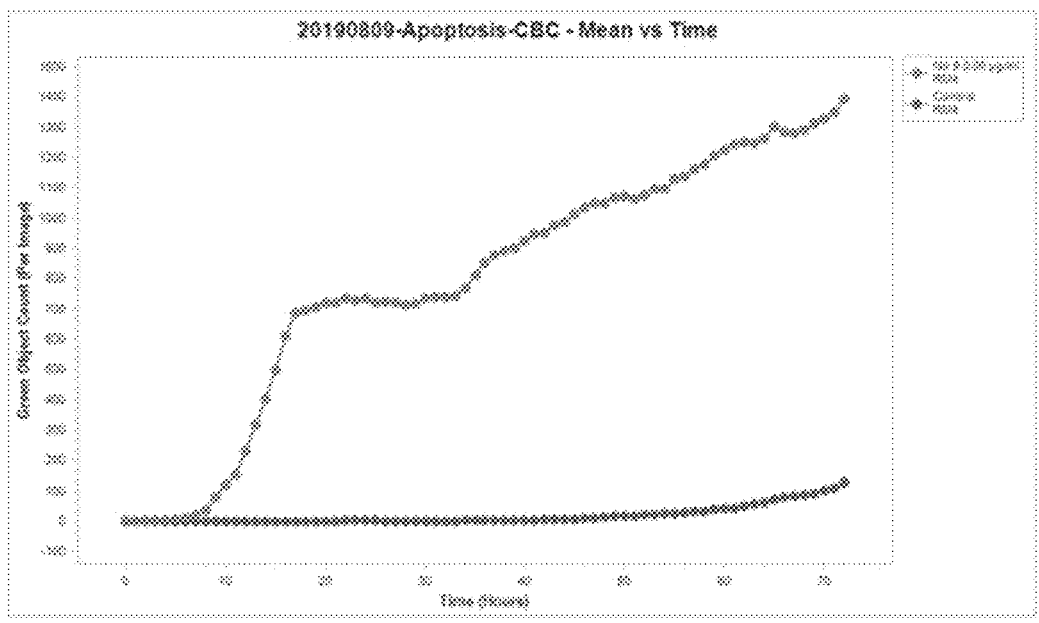
Figure 11:
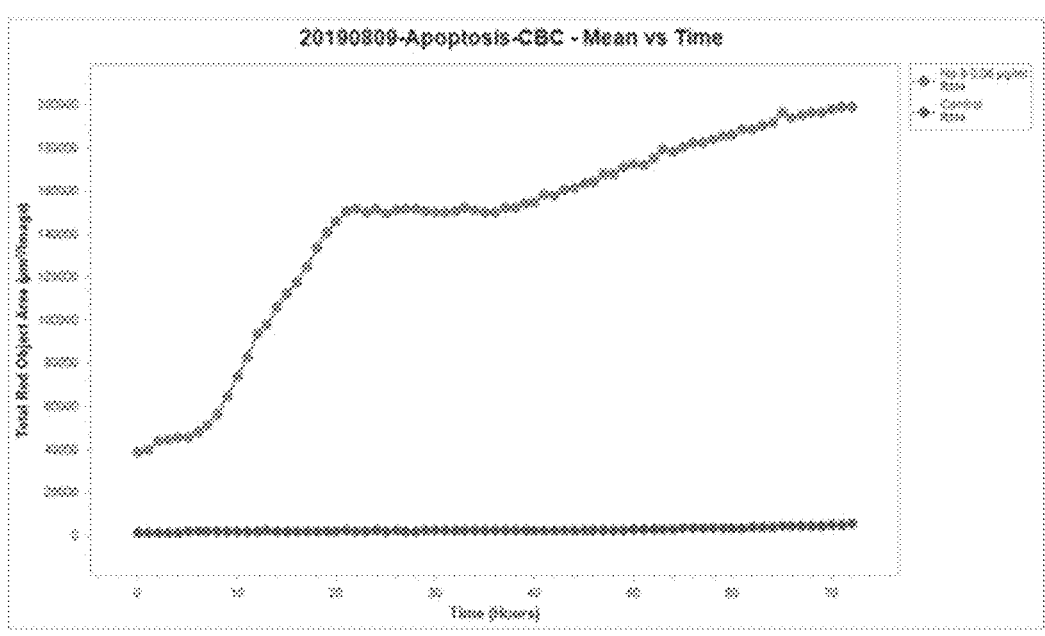

FIG. 11 is graphs showing measurements of apoptosis induction by an activation of Caspase-3/7 (A) and an activation of AnnexinV (B) in the case of the treatment of RM-4 cells by a peptide 1.

Figure 12:
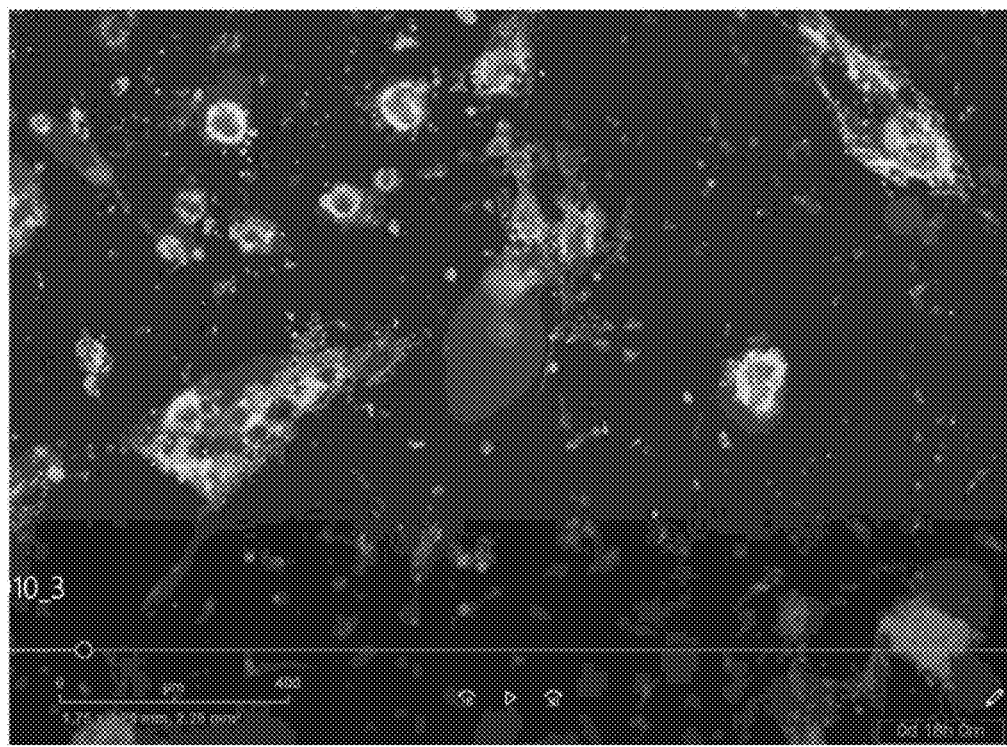

FIG. 12 is a micrograph showing an activation of Caspase-3/7 (green fluorescence) and an activation of AnnexinV (red fluorescence) after 18 hours in the case of the treatment of RM-4 cells by a peptide 1.

Figure 13:
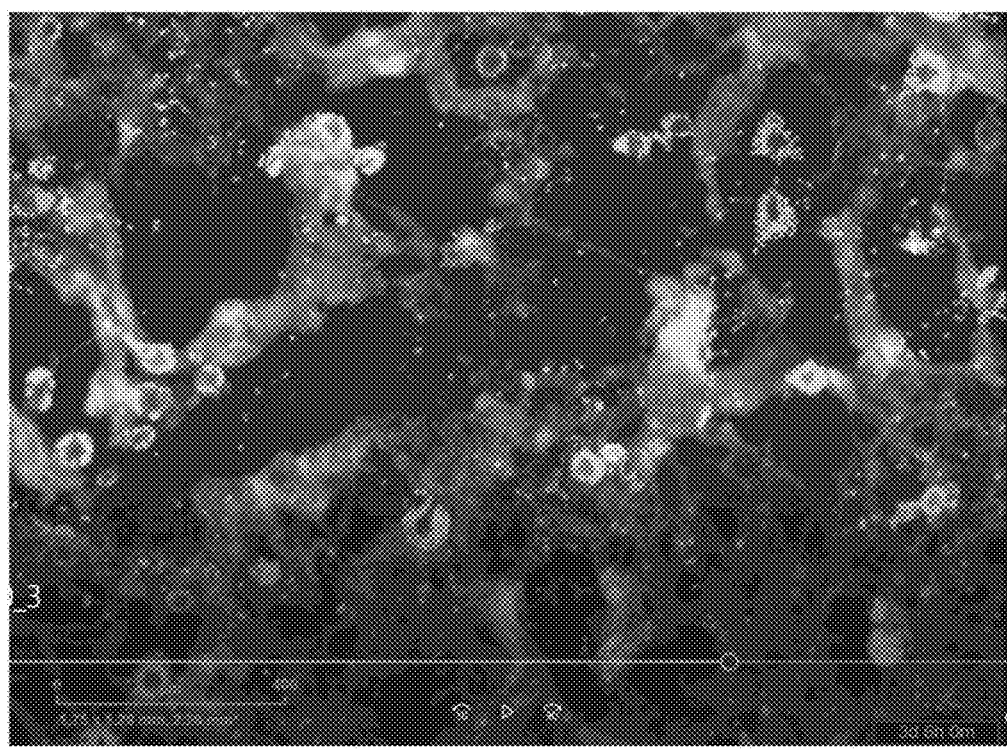

FIG. 13 is a micrograph showing an activation of Caspase-3/7 (green fluorescence) and an activation of AnnexinV (red fluorescence) after 78 hours in the case of the treatment of RM-4 cells by a peptide 1.

Figure 14:
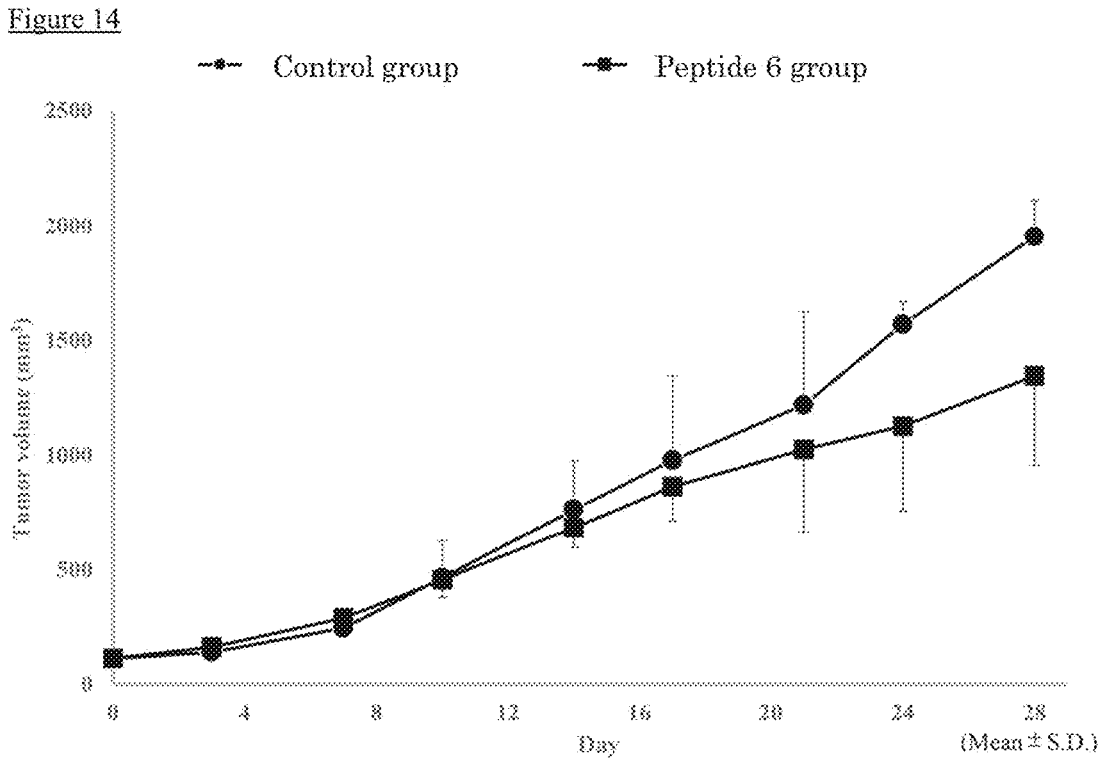

FIG. 14 is a graph showing changes in tumor volume for 28 days after transplanting cancer cells into mice and administering peptide 6.

Figure 15:
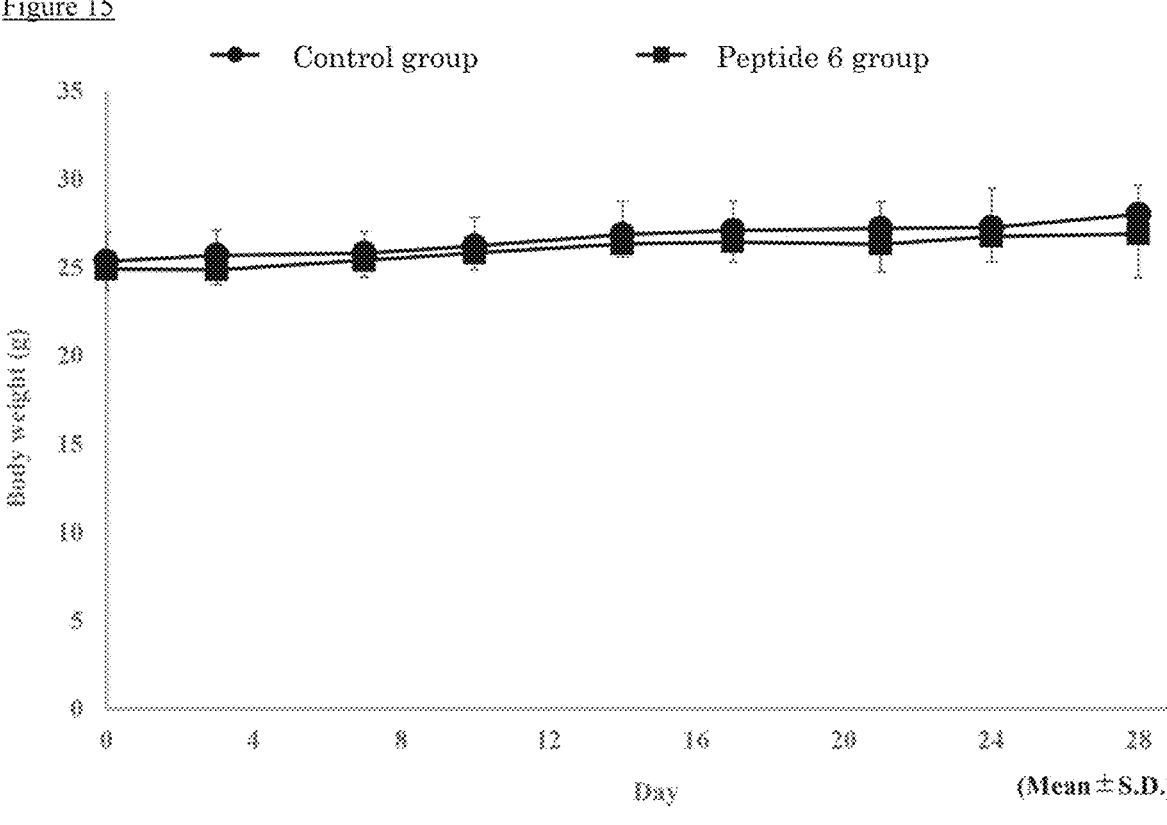

FIG. 15 is a graph showing changes of body weight for 28 days after transplanting cancer cells into mice and administering peptide 6.

Figure 16:
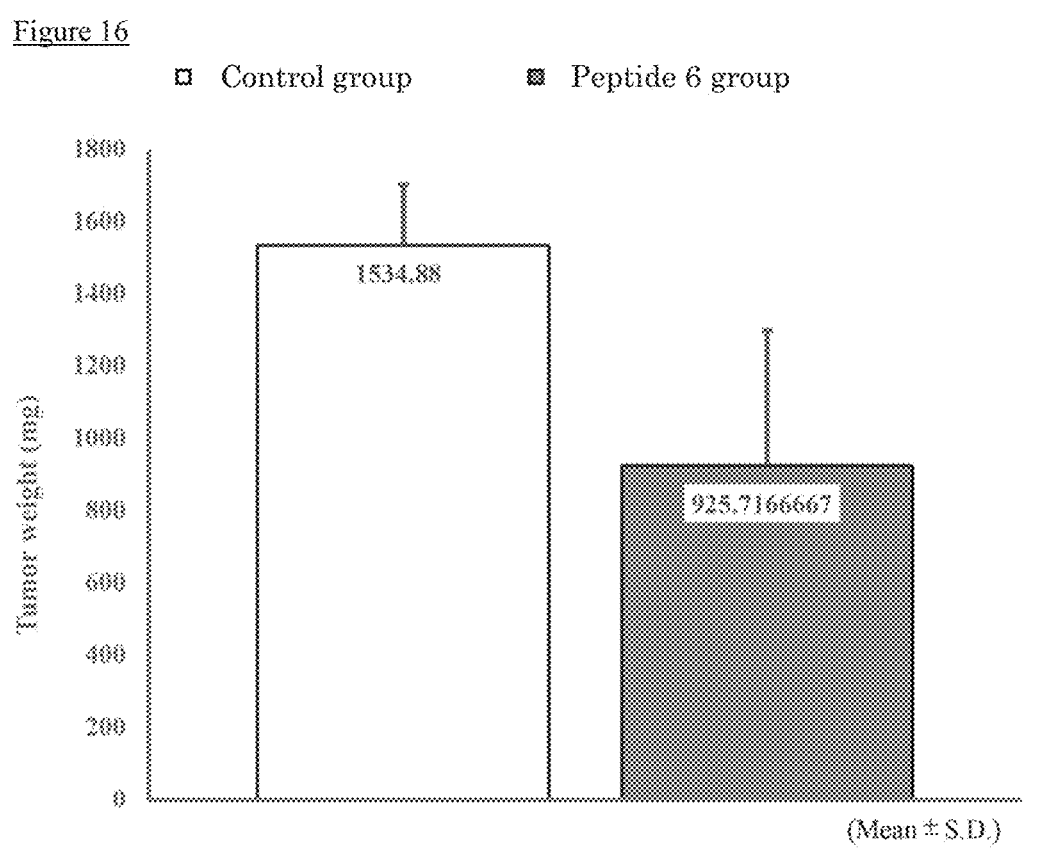

FIG. 16 is a graph showing the tumor weights of the group in which cancer cells were transplanted into mice and the peptide 6 was administered, and the control group, after 28 days.

Figure 17:
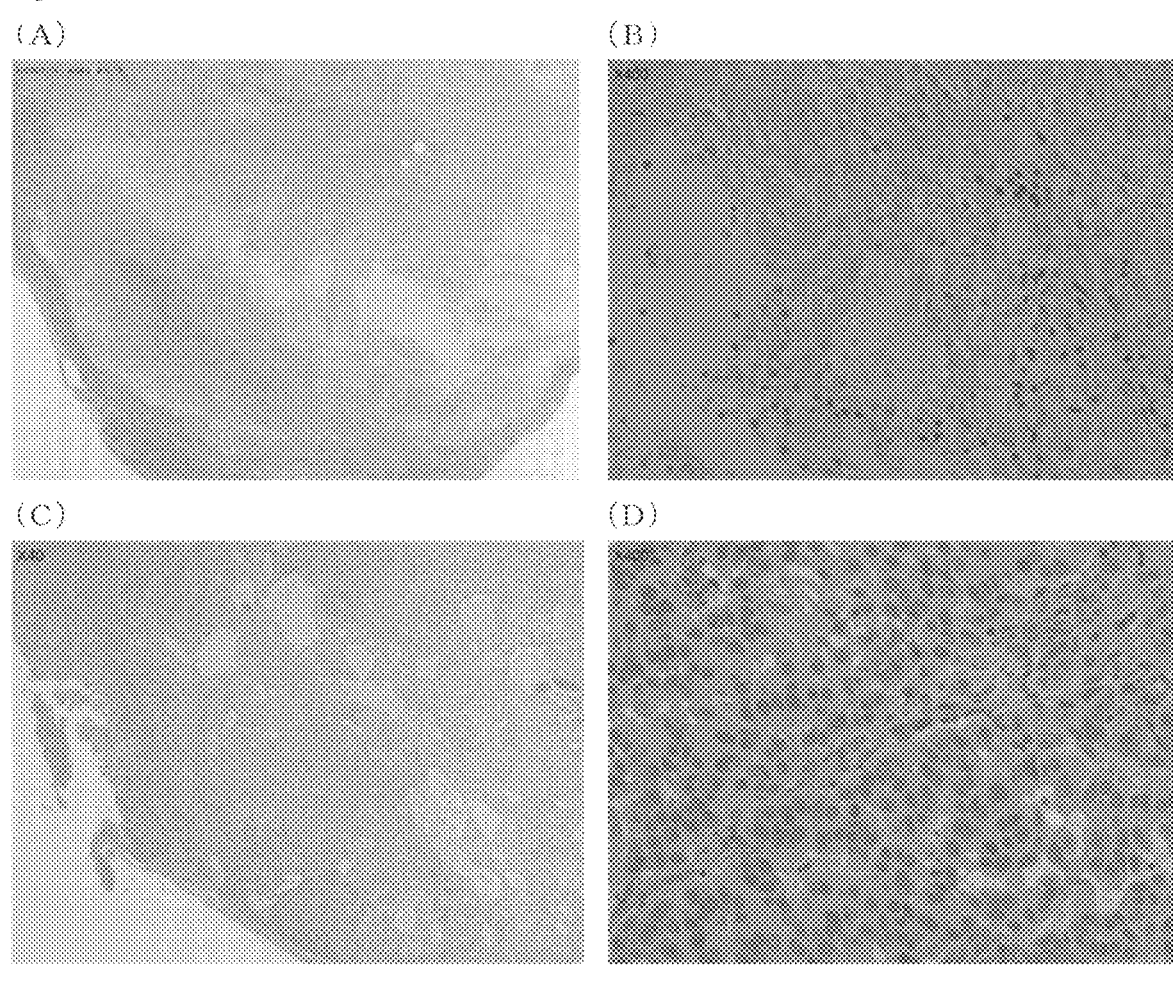

FIG. 17 is 40-fold (A) and 400-fold (B) photographs of the removed tumor mass of mice treated with peptide 6, and 40-fold (C) and 400-fold (D) photographs of the removed tumor mass of control mice.

DESCRIPTION OF EMBODIMENTS

[1] Polypeptide

A polypeptides of the present invention comprises an amino acid sequence selected from the group consisting of the amino acid sequences of SEQ ID NOs: 1 to 8. The amino acid sequences of SEQ ID NOs: 1 to 8 are as follows.

```
                                    (SEQ ID NO: 1)
    Pro-Leu-Val-Ser-Thr-Gln-Thr-Ala-Ile-Ala (SEQ ID NO: 2)
    Pro-Leu-Val-Ser-Thr-Gln-Thr-Ala-Leu-Ala (SEQ ID NO: 3)
    Pro-Leu-Val-Ser-Gln-Thr-Thr-Ala-Ile-Ala (SEQ ID NO: 4)
    Pro-Leu-Val-Ser-Gln-Thr-Thr-Ala-Leu-Ala (SEQ ID NO: 5)
    Pro-Ile-Val-Ser-Thr-Gln-Thr-Ala-Ile-Ala (SEQ ID NO: 6)
    Pro-Ile-Val-Ser-Thr-Gln-Thr-Ala-Leu-Ala (SEQ ID NO: 7)
    Pro-Ile-Val-Ser-Gln-Thr-Thr-Ala-Ile-Ala (SEQ ID NO: 8)
    Pro-Ile-Val-Ser-Gln-Thr-Thr-Ala-Leu-Ala
```

4

Further, the polypeptide of the present invention comprises an amino acid sequence in which 1 to 4 amino acids are deleted, substituted, inserted, and/or added in an amino acid sequence of SEQ ID NOs: 1 to 8, and has a cell fusion activity.

The polypeptide (1) comprising an amino acid sequence selected from the group consisting of the amino acid sequences of SEQ ID NOs: 1 to 8, comprises a polypeptide consisting of an amino acid sequence selected from the group consisting of the amino acid sequences of SEQ ID NOs: 1 to 8. Further, the polypeptide (2) comprising an amino acid sequence, in which 1 to 4 amino acids are deleted, substituted, inserted, and/or added in an amino acid sequence of SEQ ID NOs: 1 to 8, and having a cell fusion activity (hereinafter referred to as a variation functionally equivalent), comprises a polypeptide consisting of an amino acid sequence, in which 1 to 4 amino acids are deleted, substituted, inserted, and/or added in an amino acid sequence of SEQ ID NOs: 1 to 8, and having a cell fusion activity The polypeptide of the present invention can exhibit the cell fusion activity by the polypeptide consisting of sequence of ten amino acids of the amino acid sequences of SEQ ID NOs: 1 to 8 or the like, that is, the polypeptide has a specific structure for exhibiting cell fusion activity in the sequence of ten amino acids. Therefore, so long as the specific structure for exhibiting cell fusion activity in the sequence of ten amino acids is not destroyed, the polypeptide of the present invention can exhibit cell fusion activity even when other amino acid, polypeptide or protein is bonded thereto.

<<Variation Functionally Equivalent>>

The variation functionally equivalent is not particularly limited, so long as the polypeptide comprises an amino acid sequence, in which 1 to 4 amino acids, preferably 1 to 3 amino acids, more preferably 1 to 2 amino acids, most preferably one amino acid, are deleted, substituted, inserted, and/or added in one site or plural sites of an amino acid sequence of SEQ ID NOs: 1 to 8, and has a cell fusion activity.

For example, the polypeptide comprising the amino acid sequence of SEQ ID NO:2 or SEQ ID NO:5 is a variation functionally equivalent in which one amino acid is substituted with respect to the polypeptide comprising the amino acid sequence of SEQ ID NO:1. The polypeptide comprising the amino acid sequence of SEQ ID NO:3 or SEQ ID NO:6 is a variation functionally equivalent in which two amino acids are substituted with respect to the polypeptide comprising the amino acid sequence of SEQ ID NO:1. The polypeptide comprising the amino acid sequence of SEQ ID NO:4 or SEQ ID NO:7 is a variation functionally equivalent in which three amino acid are substituted with respect to the polypeptide comprising the amino acid sequence of SEQ ID NO:1. The polypeptide comprising the amino acid sequence of SEQ ID NO:8 is a variation functionally equivalent in which four amino acid are substituted with respect to the polypeptide comprising the amino acid sequence of SEQ ID NO:1.

The "deletion, substitution, insertion, and/or addition of 1 to 4 amino acids" in the variation functionally equivalent is the "conservative substitution" that may maintain the function of the polypeptide of the present invention. The "conservative substitution" is not limited, but can be carried out by replacing an amino acid residue with different amino acid residues having similar chemical properties. As the conservative substitution, there may be mentioned, for example, a substitution of a hydrophobic residue for another hydrophobic residue, or a substitution of a polar residue for another polar residue having the same charge. Amino acids which have similar chemical properties and can be conservatively substituted with each other are known to those skilled in the art. More particularly, as nonpolar (hydrophobic) amino acids, there may be mentioned, for example, alanine, valine, isoleucine, leucine, proline, tryptophan, phenylalanine, or methionine. As polar (neutral) amino acids, there may be mentioned, for example, glycine, serine, threonine, tyrosine, glutamine, asparagine, or cysteine. As basic amino acids having a positive charge, there may be mentioned, for example, arginine, histidine, or lysine. As acidic amino acids having a negative charge, there may be mentioned, for example, aspartic acid or glutamic acid. It is not limited thereto, but the variation functionally equivalent having cell fusion activity can be obtained by such "conservative substitution."

The polypeptide of the present invention is not limited, but preferably proline at N-terminus thereof is methylated. That is to say, the N-terminal proline is preferably methylated proline. The polypeptide of the present invention, is not limited to, but can exhibit an even excellent cell fusion activity due to the methylation of the N-terminal proline.

The polypeptide of the present invention can be prepared by the method known in the art. For example, although it can be obtained by culturing the transformant containing an expression vector described later, it is preferably prepared by a chemical synthesis method.

<<Cell Fusion Activity>>

The polypeptide of the present invention has the cell fusion activity. In the cell fusion of the polypeptide of the present invention, some cells are fused and a fused cell with some nuclei are formed.

In addition, apoptosis is induced in the fused cells after cell fusion, and the cells die.

<<Polynucleotide>>

The polynucleotide of the present invention is not particularly limited, as long as it encodes the polypeptide of the present invention. The term "polynucleotide" in the present specification comprises both of DNA and RNA. The polynucleotide of the present invention can be prepared, for example, by a chemical synthesis method, and the like.

<<Expression Vector>>

The expression vector of the present invention comprises the polynucleotide of the present invention. That is, the vector of the present invention is not particularly limited, as long as it comprises the polynucleotide of the present invention. For example, there may be mentioned a vector obtained by inserting the polynucleotide into a known expression vector appropriately selected according to a used host cell. The expression vector of the present invention can be constructed on the basis of a self-replicating vector (such as a plasmid), which exists as an extrachromosomal element and can replicate independently of the replication of chromosomes. Alternatively, the expression vector of the present invention may be a vector which is integrated into the genome of the host microorganism and replicated together with chromosomes, when the host is transformed with the vector. The construction of the vector of the present invention can be carried out by ordinary procedures or methods commonly used in genetic engineering.

<<Transformant>>

According to the present invention, a microorganism transformed with the expression vector is provided. A host-vector system which can be used in the present invention is not particularly limited. For example, a system utilizing *E. coli*, Actinomycetes, yeasts, filamentous fungi, or Eukaryotic cells, or a system for the expression of a fusion protein using such a microorganism can be used.

Transformation of a cell with the expression vector can be carried out in accordance with an ordinary method in this field.

In addition, the transformant can be cultured in an appropriate medium to separate and obtain the polypeptide of the present invention from the culture. According to another embodiment of the present invention, the process for producing the novel polypeptide of the present invention can be provided. Cultivation of the transformant (including culturing conditions) can be carried out in a fashion substantially similar to that of the original host used to prepare the transformant. As the method for recovering the protein of interest after the cultivation of the transformant, commonly used procedures can be carried out.

<<Antibody>>

An antibody, such as a polyclonal antibody or a monoclonal antibody, which reacts with the polypeptide of the present invention may be obtained by directly administering the polypeptide of the present invention or a fragment thereof to various animals. Alternatively, it may be obtained by a DNA vaccine method (Raz, E. et al., Proc. Natl. Acad. Sci. USA, 91, 9519-9523, 1994; or Donnelly, J. J. et al., J. Infect. Dis., 173, 314-320, 1996), using a plasmid into which a polynucleotide encoding the polypeptide of the present invention is inserted.

The polyclonal antibody may be produced from a serum or eggs of an animal such as a rabbit, a rat, a goat, or a chicken, in which the animal is immunized and sensitized by the polypeptide of the present invention or a fragment thereof emulsified in an appropriate adjuvant (for example, Freund's complete adjuvant) by intraperitoneal, subcutaneous, or intravenous administration. The polyclonal antibody may be separated and purified from the resulting serum or eggs in accordance with conventional methods for polypeptide isolation and purification. Examples of the separation and purification methods include, for example, centrifugal separation, dialysis, salting-out with ammonium sulfate, or a chromatographic technique using such as DEAE-cellulose, hydroxyapatite, protein A agarose, and the like.

The monoclonal antibody may be easily produced by those skilled in the art, according to, for example, a cell fusion method of Kohler and Milstein (Kohler, G. and Milstein, C., Nature, 256, 495-497, 1975).

A mouse is immunized intraperitoneally, subcutaneously, or intravenously several times at an interval of a few weeks by a repeated inoculation of emulsions in which the polypeptide of the present invention or a fragment thereof is emulsified into a suitable adjuvant such as Freund's complete adjuvant. Spleen cells are removed after the final immunization, and then fused with myeloma cells to prepare hybridomas.

As a myeloma cell for obtaining a hybridoma, a myeloma cell having a marker such as a deficiency in hypoxanthine-guanine phosphoribosyltransferase or thymidine kinase (for example, mouse myeloma cell line P3X63Ag8.U1) may be used. As a fusing agent, polyethylene glycol may be used. As a medium for preparation of hybridomas, for example, a commonly used medium such as an Eagle's minimum essential medium, a Dulbecco's modified minimum essential medium, or an RPMI-1640 medium may be used by adding properly 10 to 30% of a fetal bovine serum. The fused strains may be selected by a HAT selection method. A culture supernatant of the hybridomas is screened by a well-known method such as an ELISA method or an immunohistological method, to select hybridoma clones secreting the antibody of interest. The monoclonality of the selected hybridoma is guaranteed by repeating subcloning by a limiting dilution method. Antibodies in an amount which may be purified are produced by culturing the resulting hybridomas in a medium for 2 to 4 days, or in the peritoneal cavity of a pristane-pretreated BALB/c strain mouse for 10 to 20 days.

The resulting monoclonal antibodies in the culture supernatant or the ascites may be separated and purified by conventional polypeptide isolation and purification methods. Examples of the separation and purification methods include, for example, centrifugal separation, dialysis, salting-out with ammonium sulfate, or chromatographic technique using such as DEAE-cellulose, hydroxyapatite, protein A agarose, and the like.

Further, the monoclonal antibodies or the antibody fragments containing a part thereof may be produced by inserting the whole or a part of a gene encoding the monoclonal antibody into an expression vector and introducing the resulting expression vector into appropriate host cells (such as E. coli, yeast, or animal cells).

Antibody fragments comprising an active part of the antibody such as F(ab')2, Fab, Fab', or Fv may be obtained by a conventional method, for example, by digesting the separated and purified antibodies (including polyclonal antibodies and monoclonal antibodies) with a protease such as pepsin, papain, and the like, and separating and purifying the resulting fragments by standard polypeptide isolation and purification methods.

Further, an antibody which reacts to the polypeptide of the present invention may be obtained in a form of single chain Fv or Fab in accordance with a method of Clackson et al. or a method of Zebedee et al. (Clackson, T. et al., Nature, 352, 624-628, 1991; or Zebedee, S. et al., Proc. Natl. Acad. Sci. USA, 89, 3175-3179, 1992). Furthermore, a humanized antibody may be obtained by immunizing a transgenic mouse in which mouse antibody genes are substituted with human antibody genes (Lonberg, N. et al., Nature, 368, 856-859, 1994).

[2] Cell Fusion Agent

The cell fusion agent of the present invention comprises the polypeptide of the present invention as an active ingredient. The cell fusion agent of the present invention may comprise one kind of the polypeptide alone or may comprise two or more kinds of polypeptides in combination An amount of the polypeptide in the cell fusion agent is not particularly limited, but for example, 0.1 to 100% by weight, preferably 10 to 100% by weight, more preferably 30 to 90% by weight. The cell fusion agent of the present invention may comprise, as substances other than the polypeptide, carriers (such as water or buffer), fillers, diluents, preservatives, stabilizers, antiseptics, antioxidants, or the like.

The cell fusion agent of the present invention can be used for breeding of plants, preparing monoclonal antibodies, or the like. The cell fusion agent of the present invention can effectively fuse cells.

Cells to be fused by the cell fusion agent of the present invention is not particularly limited, but includes microbial cells, plant cells, or animal cells. The animal cells include nucleated cells (for example, blood cells, lymphoid cells, visceral cells) of vertebrates (for example, mammals) such as mice, rats, rabbits, guinea pigs, goats, sheep, horses, and cows, or mammal-derived cancer cells.

A temperature of cell fusion is not particularly limited, so long as the cell fusion is induced, but for example, 0 to 40°

C., preferably 10 to 38° C. A treating time is not particularly limited, but preferably 1 minute to 2 hours.

[3] Pharmaceutical Composition

The pharmaceutical composition of the present invention comprises the polypeptide of the present invention as an active ingredient. Diseases which can be prevented or treated by the pharmaceutical composition of the present invention is not particularly limited. However, the pharmaceutical composition of the present invention can fuse the cancer cells, kill cancer cells, and treat cancers. In particular, the polypeptide of the present invention can induce apoptosis to cells by cell fusion. In the fused cells, Caspase-3/7 or AnnexinV is activated, and the apoptosis is induced. The apoptosis is induced in the fused cells, and thereby it can kill cancer cells.

The cancers that can be treated by the pharmaceutical composition of the present invention include tongue cancer, gingival cancer, malignant lymphoma, malignant melanoma, maxillary cancer, nose cancer, nasal cancer, laryngeal cancer, pharyngeal cancer, glioma, meningioma, neuroblastoma, papillary adenocarcinoma of thyroid, follicular carcinoma of thyroid, medullary carcinoma of thyroid, primary lung carcinoma, squamous cell cancer, adenocarcinoma, alveolar cell cancer, large cell undifferentiated cancer, small cell undifferentiated cancer, carcinoid, testicle tumor, prostate cancer, breast cancer, mammary Paget's disease, breast sarcoma, bone tumor, thyroid cancer, gastric cancer, liver cancer, acute myeloid leukemia, acute promedullary leukemia, acute myelomonocytic leukemia, acute monocytic leukemia, acute lymphocytic leukemia, acute undifferentiated leukemia, chronic myeloid leukemia, chronic lymphocytic leukemia, adult T-cell leukemia, malignant lymphoma, multiple myeloma, primary macroglobulinemia, childhood leukemia, esophageal cancer, gastric cancer, gastric/colon leiomyosarcoma, gastric/intestinal malignant lymphoma, pancreatic/gallbladder cancer, duodenal cancer, colon cancer, primary liver cancer, hepatoblastoma, uterine carcinoma in situ, cervical squamous epithelial carcinoma, uterine adenocarcinoma, squamous epithelial carcinoma of uterine gland, adenocarcinoma of uterine body, uterine sarcoma, uterine cancer sarcoma, destructive uterine mole, malignant chorioepithelioma of uterus, malignant melanoma of uterus, ovarian cancer, mesodermal mixed tumor, kidney cancer, renal pelvis transitional cell cancer, urinary tract transitional cell cancer, bladder papillary cancer, bladder transitional cell cancer, urinary squamous epithelial carcinoma, uretheral adenocarcinoma, Wilms's tumor, rhabdomyosarcoma, fibrosarcoma, osteosarcoma, chondrosarcoma, synovial membrane sarcoma, myxosarcoma, liposarcoma, Ewing's sarcoma, cutaneous squamous cell cancer, cutaneous basal cell cancer, Bowen's disease, Paget's disease, malignant melanoma of skin, malignant mesothelial cancer, metastatic adenocarcinoma, metastatic squamous cell cancer, metastatic sarcoma, and mesothelioma.

The formulation of the pharmaceutical composition of the present invention is not limited. However, there may be mentioned oral agents, such as powders, subtle granules, granules, tablets, capsules, suspensions, emulsions, sylups, extracts, or balls; or parenteral agents, such as injections, liquid for external use, ointments, suppositorys, creams for local administration, or eye-drops.

The above oral agent can be prepared in accordance with conventional methods, using fillers, such as gelatin, alginate sodium, starch, cornstarch, saccharose, lactose, glucose, mannitol, carboxymethyl-cellulose, dextrin, polyvinyl pyrrolidone, clystalline cellulose, soy lecithin, sucrose, fatty acid ester, talc, magnesium stearate, polyethylene glycol, magnesium silicate, silicic anhydride, or synthetic aluminum silicate; binders, disintegrators, detergents, lubricants, flow accelerator, diluents, preservatives, colorants, flavors, correctives, stabilizers, humectants, antiseptics, antioxidant, or the like.

The parenteral agents include, for example, the injections. In a preparation of the injections, an aqueous solvent such as normal saline solution or Ringer solution, non-aqueous solutions such as plant oil or fatty acid ester, a tonicity agent such as glucose or sodium chloride, a solubility assisting agent, a stabilizing agent, an antiseptic agent, a suspending agent, or an emulsifying agent, may be optionally used, in addition to the active ingredient.

A dose of the pharmaceutical composition of the present invention may be appropriately determined in accordance with, for example, age, sex, body weight, or degree of symptom of each patient, the type of each active ingredient, type of each disease, route of administration, or the like, and the determined dosage can be administered orally or parenterally. For example, in the case of an adult, the intake amount of the pharmaceutical composition of the present invention is preferably 0.01 to 100 mg/kg per day as the polypeptide. The above administration method is an example, and other administration methods may be used. It is desirable that the administration method, dose, administration period, administration interval, and the like, of the pharmaceutical composition to humans are determined by a controlled clinical trial.

In addition, dosage form for administration of the mitochondrial function activator is not limited to a drug medicine. That is, it can be administered as a food and drink of various form, such as a functional food, a healthy food (including drink), or an animal food stuff.

As a method for preparing a pharmaceutical composition containing the polypeptide, known pharmaceutical preparation methods can be used except that the polypeptide is contained as an active ingredient.

The pharmaceutical composition of the present invention may contain other components. Examples of the other components include, for example, emulsifiers such as edible fats and oils, water, glycerin fatty acid ester, sucrose fatty acid ester, sorbitan fatty acid ester, propylene glycol fatty acid ester, glycerin organic acid fatty acid ester, polyglyceryl fatty acid ester, calcium stearoyl lactylate, sodium stearoyl lactate, polyoxyethylene sorbitan fatty acid ester; thickening stabilizers such as locust bean gum, carrageenan, alginic acids, pectin, xanthan gum, crystalline cellulose, carboxymethyl cellulose, methyl cellulose, agar, glucomannan, gelatin, starch, or chemical starch; salty taste agents such as salt, or potassium chloride; acidulants such as acetic acid, lactic acid, or gluconic acid; sugars or sugar alcohols; sweeteners such as stevia or aspartame; colorants such as beta-carotene, caramel, or red koji pigment; antioxidants such as tocopherol or tea extract; food materials or food additives such as flavoring agent; pH adjuster; food preservative, or shelf life improver. Further, the pharmaceutical composition may contain various vitamins, or functional materials such as coenzyme Q, plant sterol, or milk fat globule membrane. The amount of these other components is preferably 80% by mass or less, more preferably 40% by mass or less, and further preferably 20% by mass or less, as a total amount in the pharmaceutical composition of the present invention.

The pharmaceutical composition of the present invention can be administered to humans. Further, the subject to be administered may be animals other than human, that is, there may be mentioned pets such as dog, cat, rabbit, hamster, guinea pig, and squirrel; domestic animals such as cow, horse, and pig; experimental animals such as mouse and rat; animals bred in zoos, or the like.

<<Method for Treating Cancer>>

The method for treating cancer of the present invention comprises a step of administrating to a subject in need of such treatment a therapeutically effective amount of the polypeptide. That is, the polypeptide of the present invention can be used for treating cancer. The cancers can be treated by administrating to humans or animals a therapeutically effective amount of the pharmaceutical composition.

<<Polypeptide for Treating Cancer>>

The polypeptide of the present invention is for treating cancer.

The polypeptide can be used in the method for treating cancer. That is, the present specification discloses the polypeptide for treating cancer <<Use of Polypeptide for Manufacturing Pharmaceutical Composition>>

The polypeptide can be used for manufacturing pharmaceutical composition. That is, the present specification discloses the use of polypeptide for manufacturing pharmaceutical composition. The pharmaceutical composition is not limited, but it is for treating cancer.

<<Functions>>

A mechanism wherein the polypeptide of the present invention has the cell fusion activity, has not been completely elucidated, but may be presumed to be as follows. However, the present invention is not limited by the following presumption.

The polypeptide of the present invention is considered to exhibit cell fusion activity due to the structure commonly present in the amino acid sequences of SEQ ID NOs: 1-8. It is not limited, but the first proline is considered to be relatively important. On the other hand, the polypeptides in which the 2nd leucine and 9th isoleucine are substituted with each other, show cell fusion activity, and thus the 2nd and 9th amino acids are substitutable. That is, substitutions of these amino acids with other amino acids (such as valine) are likely to exhibit cell fusion activity. Further, the polypeptides in which the 5th threonine and 6th glutamine are substituted with each other, show cell fusion activity, and thus the 5th and 6th amino acids are substitutable. That is, substitutions of these amino acids (including the 4th serine and the 7th threonine) with other amino acids having similar properties, are likely to exhibit cell fusion activity. Furthermore, it is considered that the 8th alanine and 10th alanine may also show cell fusion activity even if they are replaced with amino acids having similar properties, such as glycine. In addition, the methylation of proline at the N-terminal is not essential for the cell fusion ability of each peptide and the induction of apoptosis in cancer cells. Therefore, peptides wherein one or more amino acids are added to N-terminal proline, can also exhibit cell fusion and apoptosis-inducing ability.

A mechanism wherein the polypeptide of the present invention has the anticancer effect, has not been completely elucidated, but may be presumed to be as follows. However, the present invention is not limited by the following presumption.

It is presumed that the polypeptide of the present invention can fuse cancer cells and induce apoptosis in the cells, and thereby it can kill cancer cells. In addition, the cell fusion is induced regardless of the type of cancer. Therefore, the polypeptide of the present invention is considered to be effective against many types of cancer.

EXAMPLES

The present invention now will be further illustrated by, but is by no means limited to, the following Examples.

Example 1

In this synthesis example, the peptides in which the N-terminal proline of the amino acid sequences represented by the following SEQ ID NOs:1-8 is methylated, and the peptide in which the N-terminal proline of the amino acid sequence represented by SEQ ID NO:1 is not methylated, and the peptide in which the N-terminal proline of the amino acid sequence represented by SEQ ID NO: 9 was methylated. Peptide synthesis was outsourced to Greiner/Fasmac. In connection with this, the amino acid sequence represented by SEQ ID NO:9 is an amino acid sequence in which threonine and alanine are added to the C-terminal of the amino acid sequence represented by SEQ ID NO:1.

$CH_3$-Pro-Leu-Val-Ser-Thr-Gln-Thr-Ala-Ile-Ala (hereinafter referred to as a peptide 1; SEQ ID NO:1)

$CH_3$-Pro-Leu-Val-Ser-Thr-Gln-Thr-Ala-Leu-Ala (hereinafter referred to as a peptide 2; SEQ ID NO:2)

$CH_3$-Pro-Leu-Val-Ser-Gln-Thr-Thr-Ala-Ile-Ala (hereinafter referred to as a peptide 3; SEQ ID NO:3)

$CH_3$-Pro-Leu-Val-Ser-Gln-Thr-Thr-Ala-Leu-Ala (hereinafter referred to as a peptide 4; SEQ ID NO:4)

$CH_3$-Pro-Ile-Val-Ser-Thr-Gln-Thr-Ala-Ile-Ala (hereinafter referred to as a peptide 5; SEQ ID NO:5)

$CH_3$-Pro-Ile-Val-Ser-Thr-Gln-Thr-Ala-Leu-Ala (hereinafter referred to as a peptide 6; SEQ ID NO:6)

$CH_3$-Pro-Ile-Val-Ser-Gln-Thr-Thr-Ala-Ile-Ala (hereinafter referred to as a peptide 7; SEQ ID NO:7)

$CH_3$-Pro-Ile-Val-Ser-Gln-Thr-Thr-Ala-Leu-Ala (hereinafter referred to as a peptide 8; SEQ ID NO:8)

$CH_3$-Pro-Leu-Val-Ser-Thr-Gln-Thr-Ala-Ile-Ala-Thr-Ala (hereinafter referred to as a peptide 9; SEQ ID NO:9)

Pro-Leu-Val-Ser-Thr-Gln-Thr-Ala-Ile-Ala (hereinafter referred to as a peptide 10; SEQ ID NO:1)

The amino acid synthesis was carried out by the standard 9-fluorenylmethoxycarbonyl (Fmoc) method. In particular, Fmoc amino acids were activated by HBTU/HOBT solution (HBTU: 2-(1H-Benzotriazole-1-yl)-1,1,3,3-tetramethyluroniu Hexafluorophosphate; HOBT: 1-Hydroxybenzotriazole) and the amino acids were condensed by adding DIEA (N,N'-Diisopropylethylamine).

The cutout of the synthesized amino acids from the resin was carried out as follows. TFA (trifluoroacetic acid) solution (4.125 mL TFA, 0.25 mL $H_2O$, 0.375 g phenol, 0.125 mL ethanedithiol and 0.25 mL thioanisole)) was prepared, and it was added to the resin. Then, the whole was reacted at room temperature for 2 hours and precipitated with cold ether to obtain a crude peptide.

The obtained crude peptide was purified by RP-HPLC and lyophilized. The purity of the purification was examined by HPLC and MS under the following conditions.

HPLC Conditions

A Buffer: 0.1% TFA/$H_2O$, B Buffer: 0.1% TFA/Acetonitrile

Column: SunFire C18 Column, 5 μm, 4.6×150 mm Flow rate: 1 mL/min

Wavelength: 220 nm

MALDI-TOF-MS

Example 2

In this Example, the peptide 1 obtained in Example 1 was added to RFL cells (rat lung fetal cells) or LLC cells (Lewis lung carcinoma-derived cells), and the cell fusion activity of the peptide was examined.

RFL cells or LLC cells ($2 \times 10^6$ cells) were suspended in 6 mL of RPMI-1640 medium (Wako, 189-02025) supplemented with 5% FBS (Biosera, Cat No. 015BS493) and $8 \times 10^4$ cells/0.25 mL were dispensed to each well of 24 well plate (Iwaki, 2820-024)), and cultured. The medium was removed, and a fresh medium (20 μL) and peptide 1 (1 μg/mL) were dispensed, and the cells were further cultured for 24-36 hours. After the culture was completed, the cells were fixed with methanol (Wako), and nuclear-stained with Gimza staining solution (Muto Kagaku 15003) for microscopic examination.

FIG. 1 shows the micrographs of low magnification (A and B) and high magnification (C) of RFL cells and the micrograph of LCC cells (D). In both RFL cells and LCC cells, cells are fused and fusion cells with multiple nuclei were found.

Example 3

In this Example, the cell fusion activity of the peptide 2 was examined. The procedure of Example 2 was repeated, except that the peptide 2 was used instead of the peptide 1, and the RFL cells only used.

FIG. 2 shows the micrographs of low magnification (A) and high magnification (B) of RFL cells. In RFL cells, cells are fused and fusion cells with multiple nuclei were found.

Example 4

In this Example, the cell fusion activity of the peptide 3 was examined. The procedure of Example 3 was repeated, except that the peptide 3 was used instead of the peptide 2.

Figure 3:
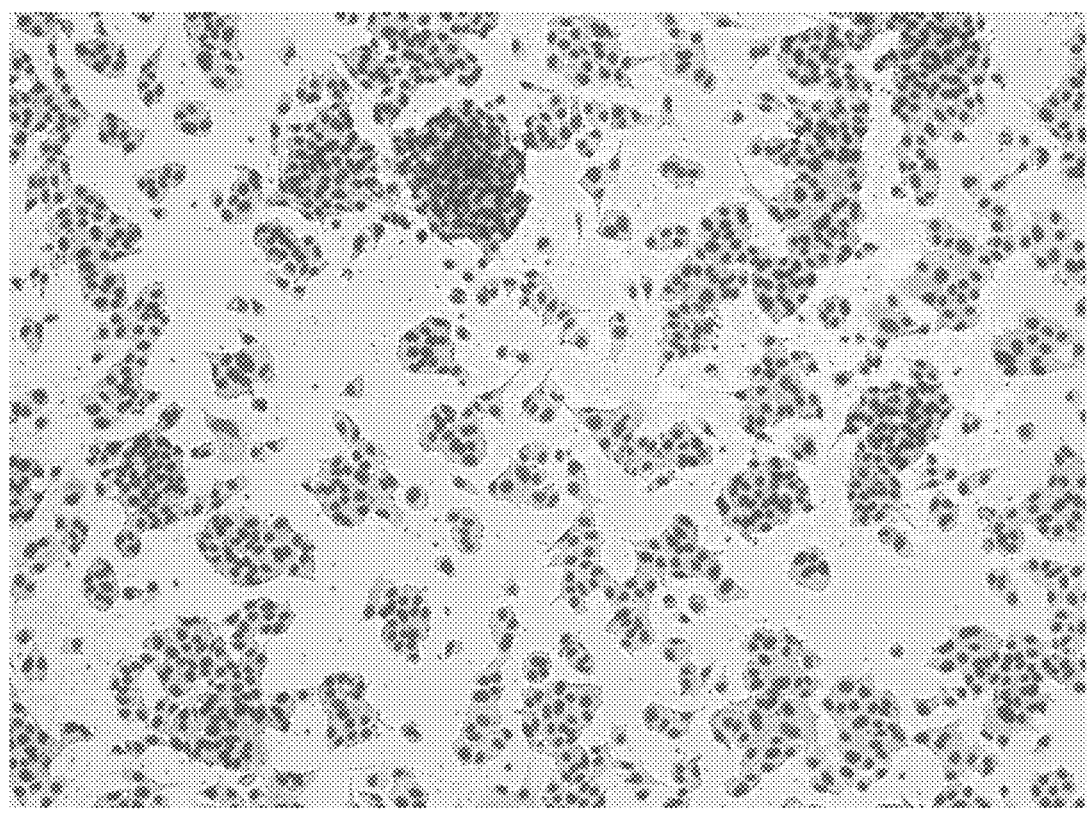
FIG. 3 is a micrograph of RFL cells (low magnification) in the case of the treatment of RFL cells by a peptide 3.

FIG. 3 shows the micrograph of low magnification of RFL cells. In RFL cells, cells are fused and fusion cells with multiple nuclei were found.

Example 5

In this Example, the cell fusion activity of the peptide 4 was examined. The procedure of Example 3 was repeated, except that the peptide 4 was used instead of the peptide 2.

Figure 4:
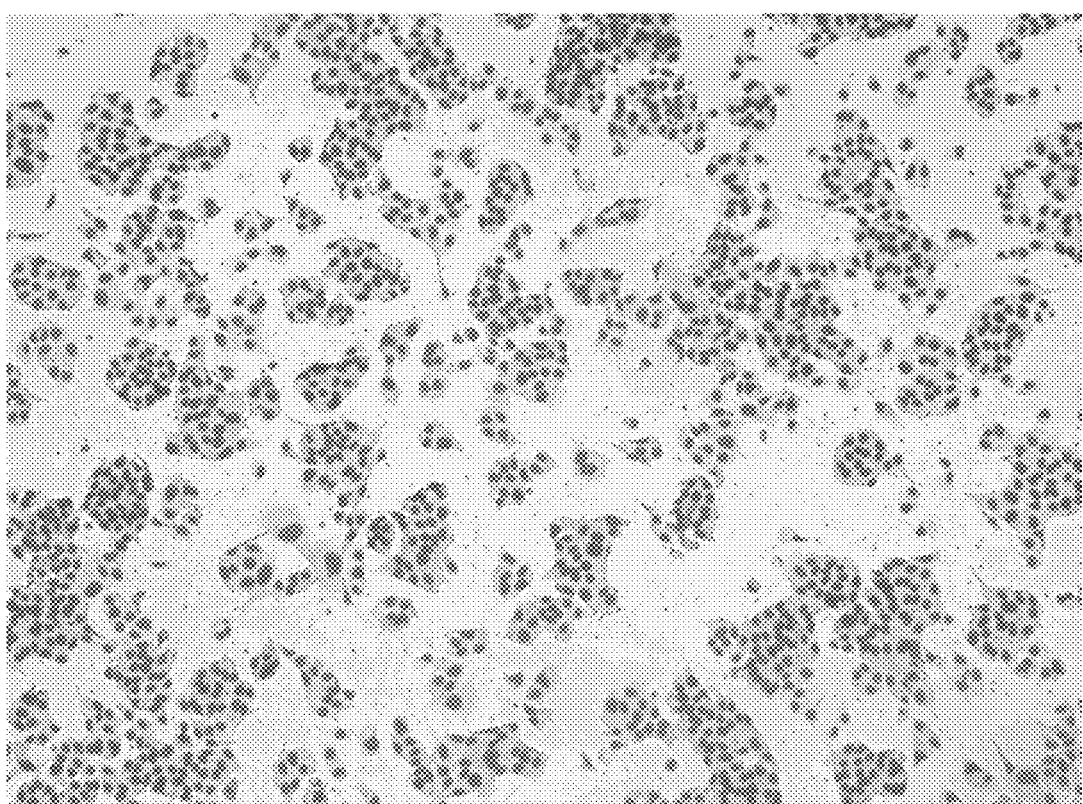
FIG. 4 is a micrograph of RFL cells (low magnification) in the case of the treatment of RFL cells by a peptide 4.

FIG. 4 shows the micrograph of low magnification of RFL cells. In RFL cells, cells are fused and fusion cells with multiple nuclei were found.

Example 6

In this Example, the cell fusion activity of the peptide 5 was examined. The procedure of Example 3 was repeated, except that the peptide 5 was used instead of the peptide 2.

Figure 5:
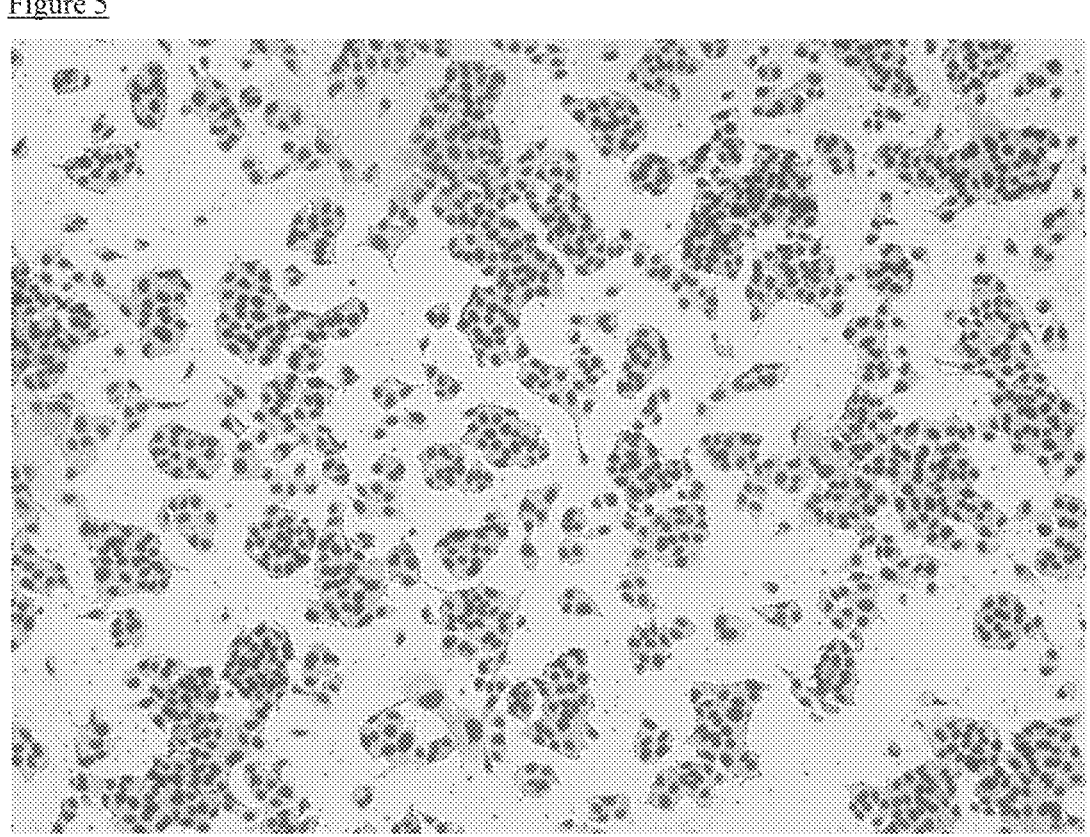
FIG. 5 is a micrograph of RFL cells (low magnification) in the case of the treatment of RFL cells by a peptide 5.

FIG. 5 shows the micrograph of low magnification of RFL cells. In RFL cells, cells are fused and fusion cells with multiple nuclei were found.

Example 7

In this Example, the cell fusion activity of the peptide 6 was examined. The procedure of Example 2 was repeated, except that the peptide 6 was used instead of the peptide 1, and the RM-4 cells only used instead of the LCC cells. In connection with this, RM-4 cells are cancer cells in which RFL cells were infected with Moloney murine leukemia virus and selected.

FIG. 6 shows the micrographs of low magnification (A) and high magnification (B) of RFL cells and the micrographs of low magnification (C and D) RM-4 cells. In RFL cells and RM-4 cells, cells are fused and fusion cells with multiple nuclei were found.

Example 8

In this Example, the cell fusion activity of the peptide 7 was examined. The procedure of Example 3 was repeated, except that the peptide 7 was used instead of the peptide 2. FIG. 7 shows the micrographs of low magnification (A) and high magnification (B) of RFL cells. In RFL cells, cells are fused and fusion cells with multiple nuclei were found.

Example 9

In this Example, the cell fusion activity of the peptide 8 was examined. The procedure of Example 2 was repeated, except that the peptide 8 was used instead of the peptide 2. FIG. 8 shows the micrographs of low magnification (A and B) and high magnification (C) of RFL cells, and the micrograph of LCC cells (D). In RFL cells and LCC cells, cells are fused and fusion cells with multiple nuclei were found.

Example 10

In this Example, the cell fusion activity of the peptide 9 was examined. The procedure of Example 3 was repeated, except that the peptide 9 was used instead of the peptide 2. FIG. 9 shows the micrograph of low magnification of RFL cells. In RFL cells, cells are fused and fusion cells with multiple nuclei were found.

The peptide 9 is the peptide in which threonine and alanine are added to the C-terminal of the amino acid sequence represented by SEQ ID NO:1. The peptide has the cell fusion activity and its cell fusion activity was superior to peptide 1.

Example 11

In this Example, the cell fusion activity of the peptide 10 was examined. The procedure of Example 3 was repeated, except that the peptide 10 was used instead of the peptide 2. FIG. 10 shows the micrograph of low magnification of RFL cells. In RFL cells, cells are fused and fusion cells with multiple nuclei were found.

That is, the peptide with normal proline (N-terminal proline of peptide 1 was not N-methylated proline), also had cell fusion activity. However, the cell fusion activity of peptide 1 seemed to be stronger.

Example 12

In this Example, the apoptosis ability of peptide 1 was examined using the RM-4 cells. An activity of Caspase-3/7 and an activity of AnnexinV (red fluorescence) which are indications of apoptosis, was measured using IncuCyte S3 live cell analysis system (Essen BioScience).

The activity of Caspase-3/7 activity is measured using an inert non-fluorescent (DEVD) substrate that can penetrate the cell membrane. An activated Caspase-3/7 cleaves the substrate, and thereby a DNA-bound green fluorescent label is released. The activity of Caspase-3/7 is measured by the intensity of green fluorescence.

The activity of Annexin V is measured using a photostable CF dye. CF dye emits a red fluorescent signal when bound to phosphatidylserine (PS). The activity of Annexin V is measured by the red fluorescent signal.

RM-4 cells were seeded on 96-well plates and 0.06 μg/mL of peptide 1 was added thereto. Caspase-3/7 Green Reagent (Unit size: 20 ul, 5 mM/vial) was diluted 500-fold with Ham's F-12K and added thereto. Then, Annexin V Red Reagent (Unit size: 100 tests/vial) was diluted 100-fold with Ham's F-12K and added thereto. They were measured using the IncuCyte S3 live cell analysis system, by continuously scanning every hour for 3 days with an objective lens of magnification of 10 times and 4 fields of view. As a control, RM-4 cells which were not treated with peptide 1, were used.

FIG. 11 (A) shows the activity of Caspase-3/7, and FIG. 11 (B) shows the activity of Annexin V. Both activities of Caspase-3/7 and Annexin V increased sharply between 10 and 20 hours, and then gradually increased. On the other hand, the activities of Caspase-3/7 and Annexin V did not increase in RM-4 cells which are not treated with peptide 1.

FIGS. 12 and 13 show fluorescence micrographs thereof after 18 and 78 hours, respectively. The treatment with peptide 1 induced apoptosis in RM-4 cells.

Example 13

In this example, the anticancer effect of peptide 6 on A549 cells (human alveolar epithelial adenocarcinoma cells) was examined in vivo.

CAnN.Cg-Foxn1nu/CrlCrlj nude mice were divided into groups of 6 animals each. A549 cells suspended in PBS at a concentration of $4 \times 10^6$ cells/mL were transplanted subcutaneously to the right ventral part thereof. The peptide 6 was administered intravenously from the tail vein at a dose of 25 mg/kg (peptide 6 group) on 14, 17, 21, 24, 28, 31, 35, and 38 days later after tumor transplantation. Control group was administered PBS only.

Tumor volume and body weight were measured every 3 or 4 days, and the tumor was resected on 38 days after tumor transplantation (on 28 days after the start of peptide administration). The tumor volume was calculated from the formula "estimated tumor volume=(minor axis)²×(major axis) ÷2" by measuring the minor axis and major axis with a caliper. One mouse in the control group had an excessively large tumor, and thus the experiment was discontinued 35 days after tumor transplantation as to one mouse. 5 mice were evaluated.

As shown in FIGS. 14 and 15, the tumor volumes were reduced by the administration of peptide 6, and therefore the peptide 6 had the anticancer effect. In addition, the administration of peptide 6 did not affect the body weight of mice, that is, exhibits no side effects, or the like.

The photographs of HE-stained excised tumors are shown in FIG. 17. FIGS. 17A (×40) and B (×400) show photographs of tumor masses of A549 cells when peptide 6 was administered, and FIGS. 17C (×40) and D (×400) show photographs of controls. In the controls, the tumor tissue mass was filled with cells. However, in the mice treated with Peptide 6, the inside of the tumor was necrotic, and it is considered that Peptide 6 showed an antitumor effect.

In the control, the tumor tissue mass is filled with cells, but in the mice treated with peptide 6, the inside of the tumor is necrotic, and thus the peptide 6 showed an antitumor effect.

INDUSTRIAL APPLICABILITY

The polypeptide of the present invention can be used for a cell fusion of plant cells, or animal cells. In addition, the pharmaceutical composition of the present invention can be used to the treatment of cancers.

The invention claimed is:

1. A polypeptide comprising an amino acid sequence selected from the group consisting of the amino acid sequences of SEQ ID NOs: 1 to 8, wherein the N-terminus of SEQ ID NO:2 is methylated.

2. The polypeptide according to claim 1, wherein the polypeptide comprises an amino acid sequence selected from SEQ ID Nos: 1 and 3-8, and the N-terminus of the polypeptide is methylated.

3. A polynucleotide encoding the polypeptide according to claim 1.

4. A vector comprising the polynucleotide according to claim 3.

5. A transformant comprising the vector according to claim 4.

6. A cell fusion agent comprising the polypeptide according to claim 1, as an active ingredient.

7. A pharmaceutical composition comprising the polypeptide according to claim 1, as an active ingredient.

8. A method for treating Lung cancer, comprising a step of administrating to a subject in need of such treatment a therapeutically effective amount of the polypeptide according to claim 1.

* * * * *